(12) United States Patent
Hong et al.

(10) Patent No.: US 11,564,995 B2
(45) Date of Patent: Jan. 31, 2023

(54) PEPTIDE-NANOPARTICLE CONJUGATES

(71) Applicant: Wisconsin Alumni Research Foundation, Madison, WI (US)

(72) Inventors: Seungpyo Hong, Madison, WI (US); Woo-jin Jeong, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 61 days.

(21) Appl. No.: 17/083,601

(22) Filed: Oct. 29, 2020

(65) Prior Publication Data

US 2021/0187120 A1    Jun. 24, 2021

Related U.S. Application Data

(63) Continuation-in-part of application No. PCT/US2019/058463, filed on Oct. 29, 2019.

(Continued)

(51) Int. Cl.
| | |
|---|---|
| A61K 47/62 | (2017.01) |
| A61K 47/60 | (2017.01) |
| A61P 37/02 | (2006.01) |
| A61K 47/69 | (2017.01) |
| A61K 9/107 | (2006.01) |
| A61K 38/17 | (2006.01) |
| A61K 47/59 | (2017.01) |

(Continued)

(52) U.S. Cl.
CPC ........ *A61K 47/6925* (2017.08); *A61K 9/1075* (2013.01); *A61K 9/1271* (2013.01); *A61K 9/5192* (2013.01); *A61K 38/1774* (2013.01); *A61K 47/595* (2017.08); *A61K 47/62* (2017.08); *A61K 47/6909* (2017.08); *A61K 47/6911* (2017.08); *A61P 35/00* (2018.01); *A61P 37/02* (2018.01)

(58) Field of Classification Search
None
See application file for complete search history.

(56) References Cited

U.S. PATENT DOCUMENTS

| | | | |
|---|---|---|---|
| 9,168,225 B2 | 10/2015 | Hong et al. | |
| 9,212,258 B2 | 12/2015 | Hong et al. | |
| (Continued) | | | |

FOREIGN PATENT DOCUMENTS

| | | |
|---|---|---|
| CN | 109464461 A | 3/2019 |
| WO | 9846270 A1 | 10/1998 |
| (Continued) | | |

OTHER PUBLICATIONS

Sinthuvanich C, Veiga AS, Gupta K, Gaspar D, Blumenthal R, Schneider JP. Anticancer β-hairpin peptides: membrane-induced folding triggers activity. Journal of the American Chemical Society. Apr. 11, 2012;134(14):6210-7. (Year: 2012).*

(Continued)

*Primary Examiner* — Nissa M Westerberg
(74) *Attorney, Agent, or Firm* — Cantor Colburn LLP

(57) ABSTRACT

Described herein is a nanoparticle system including a multivalent nanoparticle core having a plurality of β-hairpin peptides conjugated thereto. Also included are pharmaceutical compositions and methods of making the nanoparticle system. Further included are immunotherapy methods including administering the nanoparticle system to a subject in need thereof, such as a human cancer patient.

10 Claims, 25 Drawing Sheets

Specification includes a Sequence Listing.

Related U.S. Application Data

(60) Provisional application No. 62/751,831, filed on Oct. 29, 2018, provisional application No. 62/927,293, filed on Oct. 29, 2019.

(51) Int. Cl.
*A61K 9/127* (2006.01)
*A61P 35/00* (2006.01)
*A61K 9/51* (2006.01)

(56) References Cited

U.S. PATENT DOCUMENTS

| | | |
|---|---|---|
| 2013/0034559 A1 | 2/2013 | Queva et al. |
| 2014/0336368 A1 | 11/2014 | Felder-Flesch et al. |
| 2015/0368316 A1* | 12/2015 | Lazar-Molnar ............. C07K 14/70503 424/278.1 |
| 2016/0168210 A1 | 6/2016 | Ni et al. |
| 2018/0118829 A1* | 5/2018 | Mabry, III ............. C07K 16/30 |
| 2018/0221277 A1 | 8/2018 | Hong et al. |
| 2021/0393799 A1 | 12/2021 | Hong et al. |

FOREIGN PATENT DOCUMENTS

| | | |
|---|---|---|
| WO | 9847002 A2 | 10/1998 |
| WO | 2006121168 A1 | 11/2006 |
| WO | 2007005874 A3 | 1/2007 |
| WO | 2009101611 A1 | 8/2009 |
| WO | 2009114335 A3 | 9/2009 |
| WO | WO 2010027827 A3 | 3/2010 |
| WO | 2010077634 A1 | 7/2010 |
| WO | 2011066342 A3 | 6/2011 |
| WO | 2011066389 A1 | 6/2011 |
| WO | 2016025741 A1 | 2/2016 |
| WO | WO-2017123548 A1 * | 7/2017 ........... C07K 14/555 |
| WO | 2019126267 A1 | 6/2019 |
| WO | 2020092304 A1 | 5/2020 |

OTHER PUBLICATIONS

Cochran AG, Skelton NJ, Starovasnik MA. Tryptophan zippers: Stable, monomeric β-hairpins. Proceedings of the National Academy of Sciences. May 8, 2001;98(10):5578-83. (Year: 2001).*

Gupta, K. et al.; "Mechanism of Membrane Permeation Induced by Synthetic ß-Hairpin Peptides"; Biophysical Journal, vol. 105, Issue No. 9; 2013; pp. 2093-2103.

International Search Report and Written Opinion for International Application PCT/US2020/057825; International Filing Date: Oct. 29, 2020; dated Feb. 11, 2021; 21 pages.

Jeong, W. et al.; "Nanoparticle Conjugation Stabilizes and Multimerizes ß-Hairpin Peptides to Effectively Target PD-1/PD-L1 ß-Sheet-Rich Interfaces"; Journal of the American Chemical Society, vol. 142, Issue No. 4; 2020; pp. 1832-1837.

Maute, R. et al.; "Engineering high-affinity PD-1 variants for optimized imunotherapy and imuno-PET imaging" PNAS, vol. 112, Issue No. 47; 2015; pp. E6506-E6514; DOI:10.1073/pnas.1519623112.

Pascolutti, R. et al.; "Structure and Dynamics of PD-L1 and an Ultra-High-Affinity PD-1 Receptor Mutant"; Structure, vol. 24, Issue No. 10; 2016; pp. 1719-1728.

Black, M. et al.; "Activation of the PD-1/PD-L1 immune checkpoint confers tumor cell chemoresistance associated with increased metastasis", Oncotarget, vol. 7, No. 9, 2016; pp. 10557-10567.

Dubois, P. M., et al.; "Role of the transmembrane and cytoplasmic domains of surface IgM in endocytosis and signal transduction"; Eur. J. Immunol., vol. 22, 1992; pp. 851-857.

International Search Report and Written Opinion for International Application PCT/US2019/058463; International Filing Date: Oct. 29, 2019; dated Feb. 10, 2020; 21 pages.

Iwai, Y. et al.; "Involvement of PD-L1 on tumor cells in the escape from host immune system and tumor immunotherapy by PD-L1 blockade"; PNAS, vol. 99, No. 19, 2002; pp. 12293-12297.

Jiang, W. et al.; "Nanoparticle-mediated cellular response is size-dependent"; Nature Nanotechnology, vol. 3, Mar. 2008; pp. 145-150.

Keir, M. E. et al.; "PD-1 and Its Ligands in Tolerance and Immunity"; Annu. Rev. Immunol., vol. 26, 2008; pp. 677-704.

Kosmides, A. et al.; "Dual Targeting Nanoparticle Stimulates the Immune System to Inhibit Tumor Growth"; ACS Nano, vol. 11, Issue No. 6; 2017; pp. 5417-5429.

Lee et al.; "Molecular Mechanism of PD-1/PD-L1 Blockade Via Anti-PD-L1 antibodies Atezolizumab and durvalumab"; Scientific Reports, vol. 7, 5532; 2017; 12 pages; www.nature.com/scientificreports/.

Luan, Y. et al.; "A fully human monoclonal antibody targeting PD-L1 with potent anti-tumor activity"; International Immunophamnacology, vol. 31, 2016; pp. 248-256.

Miarcinkowska, M. et al.; "Conjugate of PAMAM Dendrimer, Doxorubicin and Monoclonal Antibody-Trastuzumab: The New Approach of a Well-Known Strategy"; Polymers (Basel), vol. 10, No. 187; 2018; pp. 1-11.

Mi, Y. et al.; "Abstract 978: Spatial-temporal delivery of OX40 agonist and PD-1 inhibitor using nanoparticles improves therapeutic efficacy of cancer immunotherapy"; Cancer Research, vol. 77, Issue No. 13 Supplement; 2017; doi:10.1158/1538-7445.AM2017-978.

Sun, J. et al.; "Programmable co-delivery of the immune checkpoint inhibitor NLG919 and chemotherapeutic doxorubicin via a redox responsive immunostimulatory polymeric prodrug carrier"; Acta Pharmacologica Sinica, vol. 38, 2017; pp. 823-834.

Xu, S. et al.; "PD-L1 monoclonal antibody-conjugated nanoparticles enhance drug delivery level and chemotherapy efficacy in gastric cancer cells"; International Journal of Nanomedicine, vol. 14, 2019; pp. 17-32.

Yang et al.; "PD-L1: PD-1 Interaction Contributes to the Functional Suppression of T-Cell Responses to Human Uveal Melanoma Cells in Vitro"; Invest Ophthalmol Vis Sci, vol. 49, No. 6, Jun. 2008; pp. 2518-2525.

International Search Report and Written Opinion for International Application PCT/US2021/056547; International Filing Date: Oct. 26, 2021; dated Mar. 2, 2022; 13 pages.

* cited by examiner

PEPTIDE-NANOPARTICLE CONJUGATES

CROSS-REFERENCE TO RELATED APPLICATIONS

This application is a Continuation-in Part of PCT/US2019/058463, filed on Oct. 29, 2019, which claims priority to U.S. Provisional Application Ser. No. 62/751,831, filed on Oct. 29, 2018, and also claims priority to U.S. Provisional Application 62/927,293 filed on Oct. 29, 2019, which are incorporated herein by reference in their entirety.

FIELD OF THE DISCLOSURE

The present disclosure is related to compositions and methods for the delivery of therapeutic β-hairpin peptides.

BACKGROUND

Because of their high affinity and selectivity for target materials, antibodies have been successfully employed as binding ligands for many applications including immunotherapy. However, the low thermodynamic stability and high cost of manufacturing, which are intrinsic drawbacks of proteins, have been obstacles to their routine application. Furthermore, proteins containing many surface functional groups (e.g., amine, carboxyl, hydroxyl, and sulfhydryl groups) are often not compatible with site-specific chemical reactions, which limits their use in advanced nanobiotechnological applications. One potential approach to address these problems is to implement peptides having the useful properties of small molecules and proteins. Advances in peptide design strategies, such as library screening and structure-based molecular design, has facilitated the development of artificial peptides that can outperform proteins in target binding. In addition, peptides can be synthesized through a cost-effective chemical approach, solid-phase peptide synthesis (conjugating amino acids one at a time), enabling facile and precise tuning of amino acid compositions and macromolecular topologies.

While peptides are a promising alternative to proteins, the target binding affinity of short peptides is generally lower than that of proteins. In addition, peptides often do not maintain innate folding structures when separated from their protein contexts, which significantly affects their physicochemical properties.

What is needed are new compositions and methods for the delivery of β-hairpin peptides.

BRIEF SUMMARY

In one aspect, a nanoparticle system comprises a multivalent nanoparticle core comprising a plurality of β-hairpin peptides conjugated thereto.

In another aspect, a pharmaceutical composition comprises the nanoparticle system and a pharmaceutically acceptable excipient.

In yet another aspect, a method of making a nanoparticle system comprises contacting multivalent nanoparticle cores comprising multiple reactive end groups with a composition comprising one or more β-hairpin peptides under conditions sufficient to conjugate a plurality of the β-hairpin peptides to the multivalent nanoparticle cores and provide the nanoparticle system.

In another aspect, an immunotherapy method comprises administering the nanoparticle system to a subject in need thereof.

The above-described and other features will be appreciated and understood by those skilled in the art from the following detailed description, drawings, and appended claims.

DETAILED DESCRIPTION

Described herein is a novel engineering approach for β-hairpin peptides isolated from protein surfaces (surface β-hairpin peptides, SβPs). Described herein are peptide-nanoparticle conjugates which conformationally stabilize SβPs by conjugating them to a nanoparticle scaffold, which additionally allows the peptides to exhibit a multivalent binding effect. Dendrimer-peptide conjugates (DPCs), for example, allow for stabilization of peptide structure with minimal modification to the peptide structure, particularly β-hairpin peptides. β-hairpin peptides can be stabilized by covalent crosslinking. However, chemical modifications typically complicate the peptide preparation process and, in turn, often lead to a significant decrease in synthetic yield. The introduction of inter-strand noncovalent binding is another commonly used strategy; however, it requires substantial amino acid substitutions, which potentially affects the physicochemical properties of the peptide. The nanoparticle, e.g., DPC, platform described herein presents a novel way to effectively antagonize and target β-sheet-rich protein surfaces.

Figure 23:
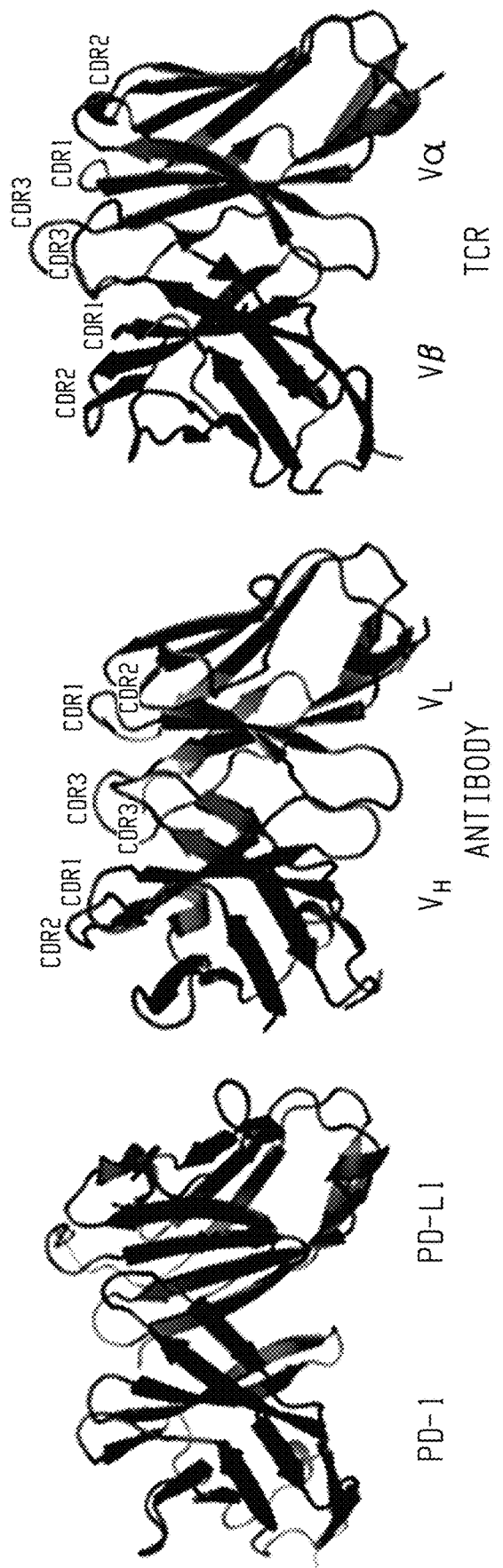
FIG. 23 shows β-sheet-rich protein-protein interaction interfaces.
Figure 24:
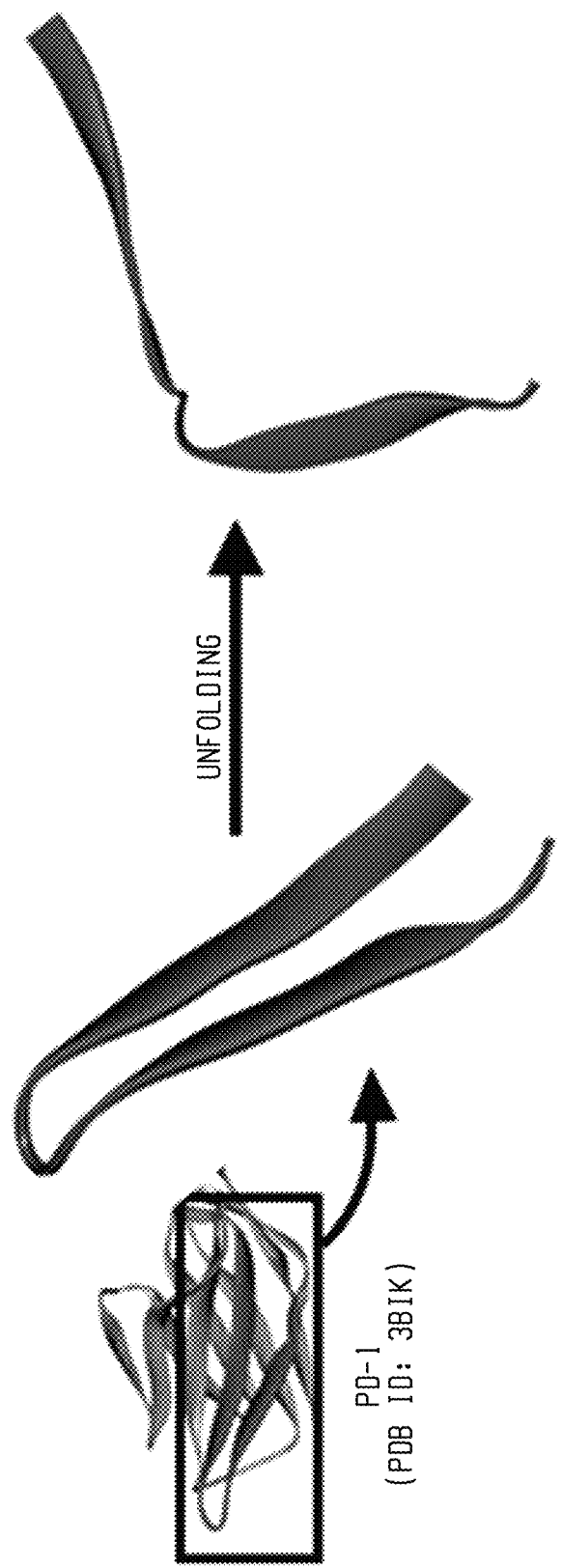
FIG. 24 shows the folding structure change of a peptide isolated from a protein context.
Figure 25:
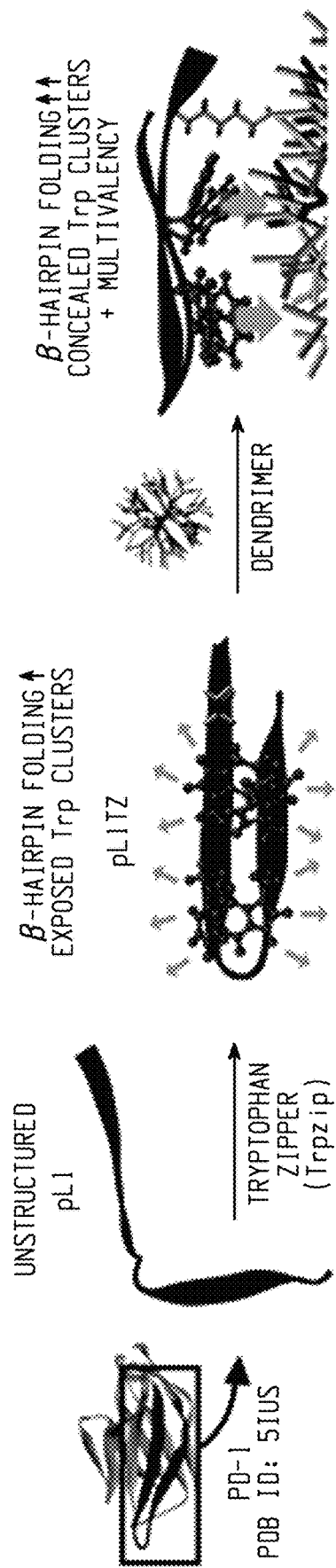
FIG. 25 shows a schematic illustration of β-hairpin stabilization by the Trpzip-DPC system.
Figure 26:
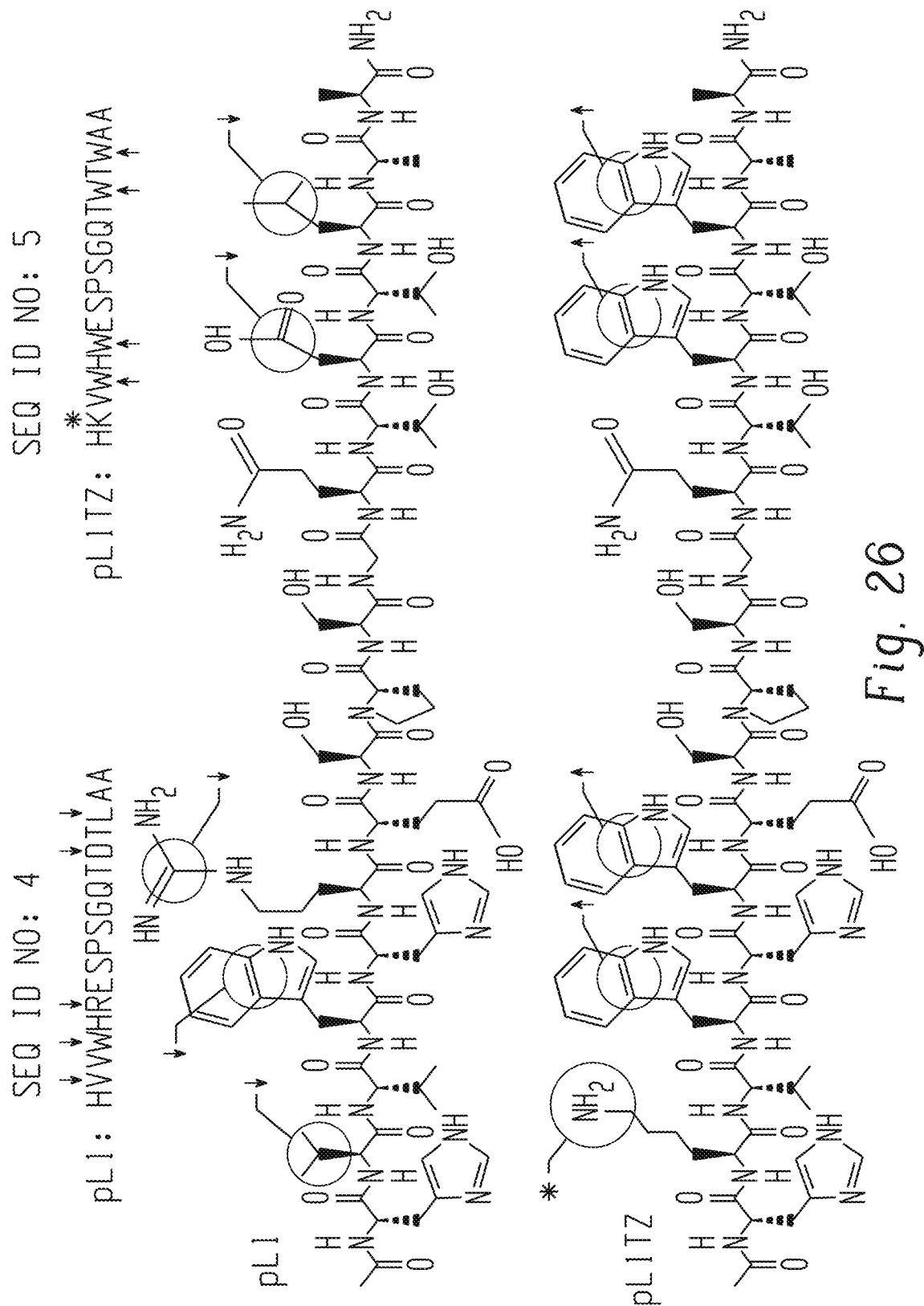
FIG. 26 shows peptide sequences and molecular structures of pL1 and pL1TZ.

The use of peptide segments on protein surfaces is an efficient approach to exploit protein functionalities. In particular, β-hairpin peptides are promising because the secondary structure is involved in a myriad of protein interactions. Based on conformational similarity, the hairpin structure also possesses potential to serve as an antagonist platform targeting β-sheet-rich protein surfaces (e.g., the PD-1/PD-L1 interface), of which wide and flat geometry is generally undruggable for small molecule drugs (FIG. 23). Because such surfaces are ubiquitous in protein-protein interactions (PPIs) and play a critical role in the progress of protein aggregation-related diseases, the regulation of PPIs mediated by β-sheet-rich surfaces has been an important and challenging issue in pharmaceutical research. However, peptide conformations are easily destabilized when isolated from protein contexts (FIG. 24), which considerably affects their target binding potency. Short plasma circulation time and vulnerability to protease digestion are other drawbacks of peptides, which has limited their widespread application.

Advantages of the nanoparticle system described herein include the use of nanoparticulate carriers with high water solubility, biocompatibility, modifiable surface groups, and multivalency.

In an embodiment, a nanoparticle system comprises a multivalent nanoparticle core comprising a plurality of 0-hairpin peptides conjugated thereto. The plurality of 0-hairpin peptides can include multiples of the same 0-hairpin peptide, or different β-hairpin peptides conjugated to the same nanoparticle core. In specific embodiments, the multivalent nanoparticle core comprises a hyperbranched polymer, a dendrimer, a dendron, a hybrid nanoparticle, or a micelle. The multivalent nanoparticle cores can have diameters of 3 to 150 nm, for example.

As used herein, hyperbranched polymers are multivalent particles that are polydisperse and irregular in terms of their branching and structure. Dendrimers, in contrast, have a very regular, radially symmetric generation structure. Dendrimers are monodisperse globular polymers which, by comparison with hyperbranched polymers, are typically prepared in multistep syntheses. The dendrimer structure is characterized by the polyfunctional core which represents the center of symmetry, various well-defined radially symmetric layers of a repeating unit (generation) and the terminal groups.

Hyperbranched polymers include polyesters, polyesteramides, polyethers, polyamides, polyethyleneimines, polyglycerols, polyglycolides, polylactides, polylactide-co-glycolides, polytartrates and polysaccharides. Hyperbranched polyesters include Boltorn® from Perstorp AB, hyperbranched polyesteramides include Hybrane® from DSM BV Niederlande, polyglycerols are produced by Hyperpolymers GmbH, and hyperbranched polyethyleneimines include Polyimin® from BASF AG.

Hyperbranched polymers also include polycaprolactones and copolymers such as poly(D,L-lactide-co-glycolides) and the polyester compounds produced by Degussa AG from the Dynapo;® S and Dynacoll® product families.

Preparation of hyperbranched polymers, e.g., hyperbranched polyglycerols, is well known in the art. For example, controlled anionic ring-opening multibranching polymerization of glycidol is performed to form hyperbranched polyglycerols. Hyperbranched polyglycerols are then reacted with succinic anhydride in pyridine to provide carboxylic acid terminal groups via an ester linkage. Once the functional group content on hyperbranched polyglycerols is verified, the hydroxyl can be further functionalized by the following scheme: hyperbranched polyglycerols-OH+N-(p-maleimidophenyl)isocyanate (PMPI, 10-fold molar excess) in DMSO or DMF at pH 8.5 to obtain hyperbranched polyglycerols-maleimide. Hyperbranched polyglycerols thus possess both carboxyl and maleimide functional groups that can react with corresponding cross-linkers and chemical groups, or can be further derivatized to suit specific functional groups available.

Amphiphilic hyperbranched polymers can form micelle-like structures. The hyperbranched polymer can be an "imperfect" molecule, in that it may include linear sections, and may feature random or unsymmetrical branching. Hyperbranched polymers can be selectively modified to achieve multiple functionalities on the surface and linked to functional components such as carbon chains to install hydrophobicity, and primary amine groups for hydrophilicity and activation for subsequent modifications.

The advantages of hyperbranched polymers include smaller unit sizes (typically <60 nm in diameter) and relatively simple procedures for synthesis. Potential disadvantages include broad size distributions and potential difficulties controlling surface modification for specific functionalities.

The term "dendrimer" as used herein includes, but is not limited to, a molecular architecture with an interior core, interior layers (or "generations") of repeating units regularly attached to and extending from this initiator core, each layer having one or more branching points, and an exterior surface of terminal groups attached to the outermost generation. Dendrimers have regular dendrimeric or "starburst" molecular structures. Nanoparticle dendrimers generally have diameters of 3 to 10 nm, for example.

Each successive dendrimer generation can be covalently bound to the previous generation. The number of reactive groups of the core structure determines n-directionality and defines the number of structures that can be attached to form the next generation.

The number of branches in a dendritic structure is dependent on the branching valency of the monomeric building blocks, including the core. For example, if the core is a primary amine, the amine nitrogen would then be divalent, resulting in a 1-2 branching motif.

Exemplary dendrimers are alkylated dendrimers such as poly(amido-amine) (PAMAM), poly(ethyleneimine) (PEI), polypropyleneimine (PPI), diaminobutane amine polypropylenimine tetramine (DAB-Am 4), polypropylamine (POPAM), polylysine, polyester, iptycene, aliphatic poly(ether), aromatic polyether dendrimers, or a combination comprising one or more of the foregoing.

The dendrimers can have carboxylic, amine and hydroxyl terminations and can be of any generation including, but not limited to, generation 1 dendrimers (G1), generation 2 dendrimers (G2), generation 3 dendrimers (G3), generation 4 dendrimers (G4), generation 5 dendrimers (G5), generation 6 dendrimers (G6), generation 7 dendrimers (G7), generation 8 dendrimers (G8), generation 9 dendrimers (G9), or generation 10 dendrimers (G10).

The PAMAM dendrimers contain internal amide bonds which may enhance their biodegradability, thus improving tolerance in terms of human therapeutic applications. The surface includes polar, highly reactive primary amine groups. The surfaces of the amino-functional PAMAM dendrimers are cationic and can be derivatized, either through ionic interactions with negatively charged molecules, or using many well-known reagents for covalent functionalization of primary amines.

When PAMAM dendrimers are employed, generations from 0 to 7 PAMAM dendrimers are typically used. For example, hybrid nanoparticles can be formed from generation 0 PAMAM dendrimers (G0); generation 1 (G1) PAMAM dendrimers; generation 2 (G2) PAMAM dendrimers; generation 3(G3) PAMAM dendrimers; generation 4 (G4) PAMAM dendrimers; generation 5 (G5) PAMAM dendrimers; generation 6 (G6) PAMAM dendrimers; or generation 7 (G7) PAMAM dendrimers. PAMAM is commercially available from multiple sources, including Sigma-Aldrich (Cat. No. 597309).

Diaminobutane amine polypropylenimine tetramine (DAB Am 4) is a polymer with a 1,4-diaminobutane core (4-carbon core) with 4 surface primary amino groups. When hybrid nanoparticles are formed from DAB-AM 4 dendrimers, generations from 0 to 7 DAB-AM 4 dendrimers are typically used. For example, hybrid nanoparticles can be formed from generation 0 DAB-AM 4 dendrimers (G0); generation 1 (G1) DAB-AM 4 dendrimers; generation 2 (G2) DAB-AM 4 dendrimers; generation 3(G3) DAB-AM 4 dendrimers; generation 4 (G4) DAB-AM 4 dendrimers; generation 5 (G5) DAB-AM 4 dendrimers; generation 6 (G6) DAB-AM 4 dendrimers; or generation 7 (G7) DAB-AM 4 dendrimers. DAB-Am 4 is commercially available from multiple sources, including Sigma-Aldrich (Cat. No. 460699).

The multivalent nanoparticles may be formed of one or more different dendrimers. Each dendrimer of the dendrimer complex may be of similar or different chemical nature than the other dendrimers (e.g., the first dendrimer can be a PAMAM dendrimer, while the second dendrimer can in be a POPAM dendrimer).

Dendrons are monodisperse, wedge-shaped dendrimer sections with multiple terminal groups and a single reactive function at the focal point. Dendrons can be grafted to a surface, another dendron, or a macromolecule, for example. Bis-MPA (bis-dimethylolpropionic acid) dendrons are available from Sigma-Aldrich.

As used herein, a "micelle" refers to an aggregate of amphiphilic molecules in an aqueous medium, having an interior core and an exterior surface, wherein the amphiphilic molecules are predominantly oriented with their hydrophobic portions forming the core and hydrophilic portions forming the exterior surface. Various monoclonal antibodies, peptides, proteins, and small molecules can covalently bind to the hydrophilic head group of micelles, covering the nanoparticle with plurality of conjugated ICIs for stronger binding kinetics. Micelles are typically in a dynamic equilibrium with the amphiphilic molecules or ions from which they are formed existing in solution in a non-aggregated form. Many amphiphilic compounds, including in particular detergents, surfactants, amphiphilic polymers, lipopolymers (such as PEG-lipids), bile salts, single-chain phospholipids and other single-chain amphiphiles, and amphipathic pharmaceutical compounds are known to spontaneously form micelles in aqueous media above certain concentration, known as critical micellization concentration, or CMC. The amphipathic, e.g., lipid, components of a micelle do not form bilayer phases, nonbilayer mesophases, isotropic liquid phases or solid amorphous or crystalline phases. The concept of a micelle, as well as the methods and conditions for their formation, are well known to skilled in the art. Micelles can co-exist in solution with lipidic particles.

Exemplary micelles include those described in U.S. Pat. No. 9,212,258, incorporated by reference for its disclosure of micelles comprising amphiphilic dendron-coils. Each amphiphilic dendron-coil comprises a non-peptidyl, hydrophobic core-forming block, a polyester dendron and a poly (ethylene) glycol (PEG) moiety. The micelles comprising amphiphilic dendron-coils are also referred to as "multivalent dendron conjugates" and "dendron-based nanomicelles (DNMs)".

The hydrophobic core-forming block of the micelles is non-peptidyl, that is, the hydrophobic core-forming block is not a peptide. In some embodiments, a micelle comprises a single type of amphiphilic dendron-coil (i.e., the amphiphilic dendron-coils in the micelle all have the same three components.) In some embodiments, a micelle comprises more than one type of amphiphilic dendron-coil (i.e., the amphiphilic dendron-coils in the micelle vary in their three components.)

In some embodiments, the non-peptidyl, hydrophobic core-forming block of the amphiphilic dendron-coil comprises polycaprolactone (PCL), poly(lactic acid) (PLA), poly(glycolic acid) (PGA) or poly(lactic-co-glycolic acid) (PLGA). In some embodiments, the non-peptidyl, hydrophobic core-forming block is PCL. In some embodiments, the PCL is poly(ε-caprolactone). In some embodiments, the non-peptidyl, hydrophobic core-forming block is PLA. In some embodiments, the non-peptidyl, hydrophobic core-forming block is PGA. In some embodiments, the non-peptidyl, hydrophobic core-forming block is PLGA. The non-peptidyl, hydrophobic core-forming block has a molecular weight including, but not limited to, a molecular weight of about 0.5 kDa to about 20 kDa. In some embodiments, the non-peptidyl, hydrophobic core-forming block is poly(ε-caprolactone) with a molecular weight of about 3.5 kDa. In some embodiments, the non-peptidyl, hydrophobic core-forming block is poly(ε-caprolactone) has a molecular weight of 14 kDa.

In some embodiments, the polyester dendron of the amphiphilic dendron-coil includes, but is not limited to, a generation 3 to generation 5, that is, a generation 3 (G3), a generation 4 (G4) or a generation 5 (G5) polyester dendron with either an acetylene or carboxylate core. In some embodiments, the polyester dendron is a G3 dendron. In some embodiments, the polyester dendron is a G5 dendron. In some embodiments, the polyester dendron has an acetylene core. In some embodiments, the polyester dendron is generation 3 polyester-8-hydroxyl-1-acetylene bis-MPA dendron. In some embodiments, the polyester dendron has a carboxylate core.

In some embodiments, the PEG moiety of the amphiphilic dendron-coil is a methoxy PEG (mPEG) moiety, amine-terminated PEG (PEG-NH$_2$) moiety, acetylated PEG (PEG-Ac) moiety, carboxylated PEG (PEG-COOH) moiety, thiol-terminated PEG (PEG-SH) moiety, N-hydroxysuccinimide-PEG (PEG-NHS) moiety, NH$_2$-PEG-NH$_2$ moiety or NH$_2$—PEG-COOH moiety. In some embodiments, the PEG moiety has a molecular weight including, but not limited to, a molecular weight from about 0.2 kDa to about 5 kDa. In some embodiments, the PEG moiety is an mPEG moiety. In some embodiments, the PEG moiety is an mPEG moiety with a molecular weight of about 2 kDa. In some embodiments, the PEG moiety is an mPEG moiety with a molecular weight of about 5 kDa.

In an embodiment, a polyester dendron is covalently modified with the linear hydrophobic polymer to help to facilitate chain entanglement and intramolecular interactions which aid in the self-assembly of core-shell type micelles and enable hydrophobic drug molecules to be loaded within the micelles. The PEG moieties form a hydrophilic corona with non-fouling properties and afford increased circulation half-life when the micelles are administered in vivo.

Biologically important properties such as biodegradability, circulation half-life, targetability, pharmacokinetics and drug release can be controlled by varying the three components (also referred to as the three polymer blocks) of the amphiphilic dendron-coils. Moreover, the copolymer structure is flexible and can be easily manipulated by varying the molecular weights of each component to fine-tune the hydrophilic-lipophilic balances (HLBs). For example, various embodiments employ PCL, polyester dendron, and PEG with molecular weights ranging 0.5-20 kDa, G3-G5 (approximately 0.9-3.5 kDa), and 0.2-5 kDa, respectively. The HLBs (20 $M_H/(M_H+M_L)$, where $M_H$ is the mass of the hydrophilic block and $M_L$ is the mass of the lipophilic block) therefore widely vary from 2.22 to 19.94.

When a dendron is co-polymerized with the hydrophobic linear polymer such as polycaprolactone (PCL), poly(lactic acid) (PLA), poly(glycolic acid) (PGA), and poly(lactic-co-glycolic acid) (PLGA) in the generation of the amphiphilic dendron-coils, the cone-shaped, amphiphilic dendron-coils in turn possess advantageous structural attributes because they form self-assembled micelles, which are thermodynamically favorable and have highly packed PEG surface layers for increased blood circulation time. The thermodynamic stability in forming micelles, along with the unique architecture that is easily tunable.

The nanocarrier systems include hybrids of hyperbranched polymers and other biocompatible nanoparticles. For example, such hybrid nanoparticles include dendrimer-liposome, dendrimer-PEG-PLA, dendrimer-exosome hybrids that combine unique advantages of dendrimers (2-10 nm in diameter) and larger nanoparticles (50-200 nm).

Exemplary hybrid nanoparticles (also referred to as nanohybrids) include those described in U.S. Pat. No. 9,168,225, incorporated herein by reference for its disclosure of hybrid nanoparticles. In this embodiment, a hybrid nanoparticle is a particle in which a nanocore is surrounded or encapsulated in a matrix or shell. In other words, a smaller particle within a larger particle. In certain embodiments, the hybrid nanoparticles comprise a nanocore inside a liposome. In other embodiments, the nanocore is surrounded by a polymeric matrix or shell (e.g., a polymeric nanoparticle).

The nanocores are preferably from 1 nm to 50 nm in their greatest diameter. More preferably, the nanocores range from 1 to 40 nm in their greatest diameter, most preferably from 3 to 20 nm in their greatest diameter. The nanocores may be analyzed by dynamic light scattering and/or scanning electron microscopy to determine the size of the particles. A nanocore can have any shape and any morphology. Examples of nanocores include nanopowders, nanoclusters, nanocrystals, nanospheres, nanofibers, and nanotubes. Given its nanoscale size, the nanocore scaffold is readily excreted. Therefore, the nanocore scaffold employed need not be biodegradable, but in particular embodiments, the nanocore scaffold is biocompatible, i.e., not toxic to cells. Scaffolds are "biocompatible" if their addition to cells in vitro results in less than or equal to 30%, 20%, 10%, 5%, or 1% cell death and do not induce inflammation or other such unwanted adverse effects in vivo.

Exemplary polymeric scaffolds include, but are not limited to, a polyamide, a polysaccharide, a polyanhydride, poly-L-lysine, a polyacrylamide, a polymethacrylate, a polypeptide, a polyethylene oxide, a polyethyleneimine (PEI), or a dendrimer such as poly(amidoamine) (PAMAM) and PAMAM(ethylenediamine-EDA) dendrimers or modified versions thereof, e.g., hydroxylated, acetylated, or carboxylated versions of said polymers. Other exemplary polymeric backbones are described, e.g., in WO98/46270 (PCT/US98/07171) or WO98/47002 (PCT/US98/06963). The multivalent polymeric scaffold molecules can have a configuration selected from linear, branched, forked or star-like.

In some embodiments, at least a portion of the multivalent polymeric scaffold molecule may be hydrophobic. In some embodiments, at least a portion of the multivalent polymeric scaffold molecule may be hydrophilic. In another embodiment, a portion of the multivalent polymeric scaffold molecule may be hydrophobic, and a different portion of the molecule may be hydrophilic. In particular embodiments, the multivalent polymeric scaffold molecule is cationic. In other embodiments, the multivalent polymeric scaffold molecule is electronically neutral. In still other embodiments, the multivalent polymeric scaffold molecule is anionic. Those skilled in the art will recognize that various starting materials may be selected to obtain a multivalent polymeric scaffold molecule that exhibits the desired properties.

In one embodiment, the shell is a liposome composed of a phospholipid such as egg phosphatidylcholine, egg phosphatidylethanolamine, soy bean phosphatidylcholine, lecithin, sphingomyelin, synthetic phosphatidylcholine, lysophosphatidylcholine, phosphatidylglycerol, phosphatidic acid, phosphatidylethanolamine, or phosphatidylserine, wherein the phospholipid can be modified with a long-circulating agent or cryoprotectant. In another embodiment, the shell is polymeric nanoparticle composed of a polymer selected from the group of poly-(γ-L-glutamylglutamine), poly-(γ-L-aspartylglutamine), poly-L-lactic acid, poly-(lactic acid-co-glycolic acid), polyalkylcyanoacrylate, polyanhydrides, polyhydroxyacids, polypropylfumerate, polyamide, polyacetal, polyether, polyester, poly(orthoester), polycyanoacrylate, [N-(2-hydroxypropyl)methacrylamide] copolymer, polyvinyl alcohol, polyurethane, polyphosphazene, polyacrylate, polyurea, polyamine polyepsilon-caprolactone, and copolymers thereof, wherein the polymer is modified or derivatized to enhance proteolytic resistance, improve circulating half-life, reduce antigenicity, reduce immunogenicity, reduce toxicity, improve solubility, or improve thermal or mechanical stability. In particular embodiments, the shell is biodegradable. In certain embodiments the multivalent polymeric scaffold is cationic and is composed of a polyamide, a polysaccharide, a polyanhydride, poly-L-lysine, a polyacrylamide, a polymethacrylate, a polypeptide, a polyethylene oxide, a polyethyleneimine, poly(amidoamine) (PAMAM) or PAMAM(ethylenediamine-EDA).

Another hybrid nanoparticle is a dendrimer-exosome hybrid as described in U.S. application Ser. No. 16/011,922. A dendrimer-exosome hybrid is an exosome loaded with one or more nanoparticle dendrimers. As used herein, exosome refers to small vesicles having a membrane structure that are secreted from various cells. Exosomes have diameters of about 25 to about 150 nm. Exosomes may express markers such as VLA-4, CD162, CXCR4, CD9, CD63, CD81 or a combination thereof. In an embodiment, the exosome is derived from a stem cell or a tumor cell which is isolated from a subject, e.g., a human subject.

In an embodiment, the exosome is derived from a stem cell or a tumor cell which is isolated from a subject, e.g., a human subject.

Stem cells include embryonic stem cells or adult stem cells, preferably, adult stem cells. The adult stem cells may be, without being limited to, mesenchymal stem cells, human tissue-derived mesenchymal stromal cells (mesenchymal stromal cell), human tissue-derived mesenchymal stem cells, multipotent stem cells, or amniotic epithelial cells, preferably, mesenchymal stem cells. The mesenchymal stem cells may be derived from, without being limited to, the umbilical cord, umbilical cord blood, bone marrow, fat, muscle, nerve, skin, amnion, placenta, and the like.

In an embodiment, the stem cell is a mesenchymal stem cell. Mesenchymal stem cells (MSCs) can specifically target inflammatory regions that are frequently found in cancerous regions, i.e., MSC tumor-homing.

In another embodiment, the exosome is isolated from a tumor cell. Tumor cells actively produce, release, and utilize exosomes to promote tumor growth.

Exosomes can be produced by isolating tumor or stem cells from a subject, expanding the tumor or stem cells to provide an expanded cell population, culturing the expanded cell population, and isolating the exosome secreted from the expanded tumor or stem cells. The internal components can be removed from the isolated exosomes to provide so-called ghost exosomes which are essentially empty vessels for loading components such as nanoparticle dendrimers. Exosomes derived from a patient can provide a non-immunogenic nanocarrier shell to the patient, in addition to the features above, allowing an option for personalized medicine.

In order to allow for conjugation of the immune checkpoint inhibitors, in one aspect, the multivalent nanoparticles are modified by reaction with alkyl epoxides, wherein the R group of the epoxide has 1 to 30 carbon atoms. In some embodiments, the alkyl epoxides react with amino groups present on the multivalent nanoparticles to form alkylated multivalent nanoparticles.

Amine groups present on the multivalent nanoparticles provide reactive sites for a variety of amine-based conjugation reactions using coupling linkers that include, but are not limited to, dicyclohexylcarbodiimide, diisopropylcarbodiimide, N-(3-Dimethylaminopropyl)-N'-ethylcarbodiimide, 1,1'-carbonyldiimidazole, N-succinimidyl S-acetylthioacetate, N-succinimidyl-S-acetylthiopropionate, 2-Mercaptoethylamine, sulfosuccinimidyl 4-(N-maleimidomethyl)cyclohexane-1-carboxylate, succinimidyl iodoacetate, succinimidyl 3-(2-pyridyldithio)propionate. In some embodiments, reactive esters are used to link multivalent nanoparticles and other compounds via ester bonds. Examples of the reactive esters include, but are not limited to, N-hydroxysuccinimide ester, N-hydroxy sulfosuccinimide ester, N-γ-maleimidobutyryl-oxysulfosuccinimide ester, nitrophenyl ester, tetrafluoro phenyl ester, pentafluorophenyl ester, thiopyridyl ester, thionitrophenyl ester. Preferably, the reactive ester group is an N-hydroxysuccinimide ester.

The nanoparticles described herein comprise a β-hairpin peptide, such as a β-hairpin peptide with high affinity for a checkpoint inhibitor receptor.

Exemplary β-hairpin peptides include tumor targeting peptides such as peptides that bind cell surface receptors, peptides that target intracellular receptors, and peptides that interact with the extracellular matrix. For example, tumor targeting peptides that bind cell surface receptors include peptides that bind integrins such as αvβ3 integrin which has an RGD binding motif, and αvβ6 integrin which is expressed on the surface of colon, liver, ovarian, pancreatic, and squamous cancer cells. Additional targets for tumor targeting peptides include aminopeptidase N, peptide transporter 1, epidermal growth factor receptors, prostate-specific membrane antigen, mucin1, urokinase plasminogen activator receptor, gastric-releasing peptide receptor, somatostatin receptor, cholecystokinin receptor, neurotensin receptor, transferrin receptor, vascular endothelial growth factor receptor, insulin, ephrin receptor, and the like. Tumor targeting peptides that bind intracellular receptors include peptides that bind BCR/ABL, a pathogenic fusion protein that is responsible for the chronic phase of chronic myelogenous leukemia (CML), cyclin A, CDK, mitochondria, and the like. Peptides that target the extracellular matrix include peptides that bind fibronectin, a fibroblast growth factor, a matrix metalloproteinase, a prostate-specific antigen, a cathepsis, and the like.

Cell penetrating peptides include R8, TAT, Transportan, and Xentry.

β-hairpin peptides such as $Z_{Aβ3}$, can be used to treat protein folding diseases such as Alzheimer's Disease, Parkinson's disease, Huntington's disease, Creutzfeldt-Jakob disease, cystic fibrosis, Gaucher's disease and many other degenerative and neurodegenerative disorders.

Immune checkpoint inhibitor β-hairpin peptides can be identified by identifying immune checkpoint inhibitor ligand peptides, e.g., surface peptides, that interact with high affinity with the immune checkpoint receptor surface. For example, surface β-hairpin PD-1 peptides which interact with PD-L1 with high affinity have been identified herein. As used herein, high affinity means $K_D$ of 0.1-1,000 nM. Such peptides can have lengths of 5 to 50 amino acids, and do not correspond to the entire immune checkpoint inhibitor.

Exemplary β-hairpin PD-1 peptides include:

```
SEQ ID NO: 1:
TYLCGAISLAPKLQIKESLRA    (βH1- wt sequence)

SEQ ID NO: 2:
TYVCGVISLAPRIQIKESLRA    (βH1- mutant sequence)

SEQ ID NO: 3:
VLNWYRMSPSNQTDRKAA       (βH2- wt sequence)

SEQ ID NO: 4:
HVVWHRESPSGQTDTKAA       (βH2- wt sequence)
```

In an aspect, the β-hairpin peptide comprises a tryptophan zipper. The tryptophan zipper analog of SEQ ID NO: 4 is SEQ ID NO: 5.

```
SEQ ID NO: 5:
HKVWHWESPSGQWDTWAA    (Trp-Zip βH2 mutant sequence)
```

As used herein, a tryptophan zipper is a β-hairpin peptide comprising four tryptophan residues disposed on the same peptide surface which cluster and stabilize the β-hairpin peptide.

The trpzip strategy (e.g., the stabilization of the folded structure of the peptides), in addition to conjugation to the nanoparticle, further improves the binding kinetics of the beta-hairpin peptides due to the stabilization of the folded structure of the peptides on the surface of the nanoparticles, e.g., the dendrimers. The intermolecular forces, including hydrogen bonding, van der Waals forces, dipolar interactions, between peptides and nanoparticle surfaces also contribute to stabilization of the folded structure of the peptides, thereby improving overall binding kinetics.

The large number of end groups on the multivalent nanoparticle core allows for conjugation of a wide variety of molecules in addition to the β-hairpin peptides. The multivalent nanoparticle core can be associated with, e.g., complexed or conjugated with, one or more of a therapeutic, prophylactic or diagnostic agent. Diagnostic agents include imaging agents.

In one aspect, the therapeutic agent is a chemotherapeutic agent. Chemotherapeutic agents include, but are not limited to, the following classes: alkylating agents, antimetabolites, anthracyclines, plant alkaloids, topoisomerase inhibitors, monoclonal antibodies, and other anti-tumor agents. In addition to the chemotherapeutic drugs described above, namely doxorubicin, paclitaxel, other suitable chemotherapy drugs include tyrosine kinase inhibitor imatinib mesylate (Gleeve® or Glivec®), cisplatin, carboplatin, oxaliplatin, mechloethamine, cyclophosphamide, chlorambucil, azathioprine, mercaptopurine, pyrimidine, vincristine, vinblastine, vinorelbine, vindesine, podophyllotoxin (L01CB), etoposide, docetaxel, topoisomerase inhibitors (L01CB and L01XX) irinotecan, topotecan, amsacrine, etoposide, etoposide phosphate, teniposide, dactinomycin, lonidamine, and monoclonal antibodies, such as trastuzumab (Herceptin®), cetuximab, bevacizumab and rituximab (Rituxan®), among others.

Other examples of therapeutic agents include, but are not limited to, antimicrobial agents, analgesics, anti-inflammatory agents, and others. Antibiotics can be incorporated into the particle, such as vancomycin, which is frequently used to treat infections, including those due to methicillin resistant staph *aureus* (MRSA). The particle optionally includes cyclosporin, a lipophilic drug that is an immunosuppressant agent, widely used post-allogeneic organ transplant to reduce the activity of the patient's immune system and the risk of organ rejection (marketed by Novartis under the brand names Sandimmune® and Neoral®). Particles comprising cyclosporine can be used in topical emulsions for treating keratoconjunctivitis sicca, as well. In this regard, particles with multifunctional surface domains incorporating such drugs can be designed to deliver equivalent dosages of the various drugs directly to the cancer cells, thus potentially minimizing the amount delivered generally to the patient and minimizing collateral damage to other tissues.

Therapeutic agents also include therapeutic nucleic acids such as gene-silencing agents, gene-regulating agents, antisense agents, peptide nucleic acid agents, ribozyme agents, RNA agents, and DNA agents. Nucleic acid therapeutic agents include single stranded or double-stranded RNA or DNA, specifically RNA, such as triplex oligonucleotides, ribozymes, aptamers, small interfering RNA including siRNA (short interfering RNA) and shRNA (short hairpin RNA), antisense RNA, microRNAs (miRNAs), or a portion thereof, or an analog or mimetic thereof, that is capable of reducing or inhibiting the expression of a target gene or sequence. Inhibitory nucleic acids can act by, for example, mediating the degradation or inhibiting the translation of mRNAs which are complementary to the interfering RNA sequence.

Diagnostic agents are agents that enable the detection or imaging of a tissue or disease. Examples of diagnostic agents include, but are not limited to, radiolabels, fluorophores and dyes.

Imaging agent refers to a label that is attached to the random copolymer of the present invention for imaging a tumor, organ, or tissue in a subject. Examples of imaging agents include, without limitation, radionuclides, fluorophores such as fluorescein, rhodamine, isothiocyanates (TRITC, FITC), Texas Red, Cy2, Cy3, Cy5, APC, and the AlexaFluor® (Invitrogen, Carlsbad, Calif.) range of fluorophores, antibodies, gadolinium, gold, nanomaterials, horseradish peroxidase, alkaline phosphatase, derivatives thereof, and mixtures thereof.

Radiolabel refers to a nuclide that exhibits radioactivity. A "nuclide" refers to a type of atom specified by its atomic number, atomic mass, and energy state, such as carbon 14 ($^{14}C$). "Radioactivity" refers to the radiation, including alpha particles, beta particles, nucleons, electrons, positrons, neutrinos, and gamma rays, emitted by a radioactive substance.

Administration of a prophylactic agent can occur prior to the manifestation of symptoms characteristic of the disease or disorder, such that the disease or disorder is prevented or, alternatively, delayed in its progression.

Therapeutic molecules, diagnostic agents, and prophylactic agents may be combined with multivalent nanoparticle core via chemical conjugation, physical encapsulation, and/or electrostatic interaction methods.

Also included are pharmaceutical compositions comprising the nanoparticle system described herein. Pharmaceutical compositions may further comprise the therapeutic, prophylactic or diagnostic agent as described above.

As used herein, "pharmaceutical composition" means therapeutically effective amounts of the nanoparticles together with a pharmaceutically acceptable excipient, such as diluents, preservatives, solubilizers, emulsifiers, and adjuvants. As used herein "pharmaceutically acceptable excipients" are well known to those skilled in the art.

Tablets and capsules for oral administration may be in unit dose form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavoring or coloring agents.

For topical application to the skin, the drug may be made up into a cream, lotion or ointment. Cream or ointment formulations which may be used for the drug are conventional formulations well known in the art. Topical administration includes transdermal formulations such as patches.

For topical application to the eye, the inhibitor may be made up into a solution or suspension in a suitable sterile aqueous or non-aqueous vehicle. Additives, for instance buffers such as sodium metabisulphite or disodium edeate; preservatives including bactericidal and fungicidal agents such as phenyl mercuric acetate or nitrate, benzalkonium chloride or chlorhexidine, and thickening agents such as hypromellose may also be included.

The active ingredient may also be administered parenterally in a sterile medium, either subcutaneously, or intravenously, or intramuscularly, or intrasternally, or by infusion techniques, in the form of sterile injectable aqueous or oleaginous suspensions. Depending on the vehicle and concentration used, the drug can either be suspended or dissolved in the vehicle. Advantageously, adjuvants such as a local anesthetics, preservative and buffering agents can be dissolved in the vehicle.

Pharmaceutical compositions may conveniently be presented in unit dosage form and may be prepared by any of the methods well known in the art of pharmacy. The term "unit dosage" or "unit dose" means a predetermined amount of the active ingredient sufficient to be effective for treating an indicated activity or condition. Making each type of pharmaceutical composition includes the step of bringing the active compound into association with a carrier and one or more optional accessory ingredients. In general, the formulations are prepared by uniformly and intimately bringing the active compound into association with a liquid or solid carrier and then, if necessary, shaping the product into the desired unit dosage form.

In an aspect, a method of making a nanoparticle system comprises contacting the multivalent nanoparticle cores comprising multiple reactive end groups with a composition comprising immune checkpoint inhibitors under conditions sufficient to conjugate a plurality of immune checkpoint inhibitors to the multivalent nanoparticle cores and provide the nanoparticle system. Exemplary end groups include coupling linkers and reactive epoxides, such as dicyclohexylcarbodiimide, diisopropylcarbodiimide, N-(3-dimethylaminopropyl)-N'-ethylcarbodiimide, 1,1'-carbonyldiimidazole, N-succinimidyl S-acetylthioacetate, N-succinimidyl-S-acetylthiopropionate, 2-Mercaptoethylamine, sulfosuccinimidyl 4-(N-maleimidomethyl)cyclohexane-1-carboxylate, succinimidyl iodoacetate, succinimidyl 3-(2-pyridyldithio)propionate, N-hydroxysuccinimide ester, N-hydroxy sulfosuccinimide ester, N-γ-maleimidobutyryl-oxysulfosuccinimide ester, nitrophenyl ester, tetrafluoro phenyl ester, pentafluorophenyl ester, thiopyridyl ester, thionitrophenyl ester, and combinations comprising at least one of the foregoing.

In an embodiment, the multivalent nanoparticle cores comprise two or more different types of reactive end groups to enhance the reactivity and/or specificity of the cores.

In another embodiment, an immunotherapy method comprises administering to the subject, e.g., a human subject, a nanoparticle system as described herein. Exemplary human subjects include cancer patients and patients with immune disorders such as multiple sclerosis and rheumatoid arthritis. The nanoparticles can target the immune system by interacting with T cells, cancer cells and/or antigen presenting cells.

When the β-hairpin peptides are immune checkpoint inhibitor peptides, the compositions and methods described herein are applicable to all cancers including solid tumor cancers, e.g., those of the breast, prostate, ovaries, lungs and brain, and liquid cancers such as leukemias and lymphomas.

The methods described herein can be further combined with additional cancer therapies such as radiation therapy, chemotherapy, surgery, and combinations thereof.

The invention is further illustrated by the following non-limiting examples.

EXAMPLES

Example 1: Synthesis and Analysis of PD-1/PD-L1 Peptide Inhibitor Complex

Materials and Methods

Peptide Synthesis. Fmoc-amino acids and coupling reagents were purchased from Anaspec (U.S.A) and Novabiochem (Germany), while general chemicals were obtained from Sigma-Aldrich (U.S.A). Rink Amid MBHA resin LL (Novabiochem, Germany) was used as the scaffold for peptide synthesis. Sequences were synthesized using standard amino acids with a standard Fmoc protecting group. Final deprotection and cleavage of the peptide from resin involved treating the resin-bound peptide with a cleavage cocktail (trifluoroacetic acid (TFA):thioanisole:ethanedithiol (EDT) at a ratio of 95:2.5:2.5) for 2 h and was followed by precipitation with tert-butyl methyl ether. Peptides were purified using reverse-phase HPLC (mobile phase of water/acetonitrile with 0.1% TFA). Peptide molecular weight was quantified by matrix-assisted laser desorption/ionization time-of-flight (MALDI-TOF) mass spectrometry (AXIMA™, Shimadzu, Japan) with α-Cyano-4-hydroxycinnamic acid (CHCA) as the matrix. Peptide concentration was quantified by ultraviolet-visible (UV-Vis) spectrophotometry in water/acetonitrile (1:1) using the molar extinction coefficient for tryptophan (5500 $M^{-1}$ $cm^{-1}$) and tyrosine (1280 $M^{-1}$ $cm^{-1}$) at 280 nm.

Dendrimer-peptide Conjugate (DPC) Preparation. G7 PAMAM dendrimers (10 mg) (Dendritech, U.S.A) dissolved in 1 mlL of methanol were acetylated by the addition of acetic anhydride at 60, 80, and 90% equivalence for the number of amine groups on the dendrimer surface, along with triethylamine (TEA) at 600 molar excess of the dendrimers. The reaction was done under vigorous stirring and at room temperature for 24 h. Excess reagents were removed using a Vivaspin™ Turbo 15 (MWCO 10,000, Sartorius, Germany) at 4,000 r.p.m. for 15 min and washing with dd$H_2O$ 10 times (centrifugal filtration). Acetylated dendrimers were then fluorescently labeled using N-hydroxysuccinimide rhodamine (NHS-RHO) to better quantify and visualize the nanoparticles. Dendrimers were dissolved in dimethylsulfoxide (DMSO), NHS-RHO dissolved in DMSO at 10 eq for the number of the dendrimers was added in dropwise, and then the reaction was carried out at room temperature for 24 h. Excess reagents were removed by the centrifugal filtration. NHS-RHO labelled dendrimers were then conjugated with the peptides. Dendrimers were dissolved in phosphate buffered saline (PBS, pH 7.4) and then 1-Ethyl-3-(3-dimethylaminopropyl)-carbodiimide (EDC) and NHS dissolved in PBS were added to the dendrimer solution. The solution was then vigorously stirred at RT for 1 h. Afterwards, peptides dissolved in PBS were added, and then the reaction proceeded at room temperature for 24 h. Excess peptides and reagents were removed by the centrifugal filtration.

Surface plasma resonance (SPR). SPR analysis was done using a BIAcore™ X (Pharmacia Biosensor AB, Uppsala, Sweden). In short, PD-L1 proteins (R&D systems) were immobilized onto carboxylated dextran-coated gold film surface of sensor chip (CM5 sensor chip, GE Healthcare) through EDC/NHS chemistry. 30 µL of sample solution was injected at a flow rate of 20 L/min. Sample solution was allowed to flow into both channels (channel 1 for reference, channel 2 with PD-L1), and the final SPR sensorgrams were obtained by subtracting the channel 2 signal from those of channel 1.

Circular Dichroism (CD) Spectroscopy. CD spectra were obtained using an Aviv model 420 Circular Dichroism spectrometer (Aviv, U.S.A.). Samples were analyzed from 260 to 190 nm using a 1 mm path length quartz cuvette.

Attenuated Total Reflection-Fourier Transform Infrared (ATR-FTIR) Spectroscopy. Samples dissolved in $H_2O$ were dried on a ZnSe ATR prism. FTIR spectra were obtained on a Bruker Equinox 55/S FTIR spectrometer.

Molecular dynamics (MD) simulation study. The systems were simulated with NAMD and the CHARMM force field (CHARMM General Force Field and CHARMM36) in an NPT ensemble at P=1 bar and T=300 K, using Langevin dynamics with a damping constant of 0.01 ps-1 and a time step of 2 fs. Long-range electrostatic interactions were calculated by the PME method in the presence of periodic boundary conditions. The H-bonds number was analyzed by VMD with a cutoff distance of 3.5 Å and angle of 60°.

Fluorescence polarization (FP) assay. FP assay in PBS was used the PD-L1 binding and competition assays (λex=480 nm; λem=535 nm). Fluorescence anisotropy measurements were performed at room temperature, in a 384-well plate, and using an Infinite® M1000 Pro microplate reader (Tecan). A fβH2_mt/PD-L1 complex was used for the FP competition assay after 30 min incubation time and titrated with the competitors.

Cell culture. Human renal cell carcinoma (RCC) cell line, 786-O, and breast cancer cell line, MCF-7, were utilized as high- and low-PD-L1 expressing cancer cell models, respectively. The human T lymphocyte cell line, Jurkat, was used in this study as a representative PD-1-expressing immune cells. 786-O and Jurkat T cells were cultured in RPMI media, while MCF-7 cells were grown in DMEM media. All cell culture media were supplemented with 1% (v/v) penicillin/streptomycin (P/S) and 10% (v/v) fetal bovine serum (FBS). Cells were incubated under humidified atmosphere containing 5% $CO_2$ at 37° C.

Western Blot. The total protein lysate from 786-O and MCF-7 cells were prepared by incubating the cells with RIPA buffer (150 mM NaCl, 1% NP-40, 1% sodium deoxycholate, 0.1% SDS, 50 mM Tris-HCl, pH 7.5, 2 mM EDTA, Protease Inhibitor Cocktail II). The protein content of the lysate was quantified by BCA Assay (Pierce™ BCA Protein Assay Kit). 25 g of proteins were resolved on a 4-16% gradient acrylamide gel and transferred onto PVDF membrane in wet transfer conditions. The blot was probed overnight with primary antibody against PD-L1 (polyclonal anti human PD-L1, AF156, R&D Systems) and beta-Actin (monoclonal anti-beta-Actin, MAB8929, R&D Systems) at 4° C. followed by incubation with appropriate secondary antibodies for 1 hour at room temperature. The proteins on the blot were detected using chemiluminescent reagent, Clarity™ Western ECL Substrate (Bio-Rad) and imaged using Syngene™ G:Box F3 (Syngene, Frederick, Md.).

Assessment of T cell Cytokine Production. Activity of Jurkat T cells were investigated in cancer-immune cell co-culture system by assessing the amount of interleukin-2 (IL-2) secreted by T cells using ELISA. Cancer cells were incubated in 96-well plates (5,000 cells/well) for 48 h. Cancer cells and T cells were pre-treated with interferon-γ (IFNγ, 10 ng/mL) and phytohaemagglutinin (PHA, 1 µg/mL)/phorbol myristate acetate (PMA, 50 ng/mL) for 30 h in order to activate PD-L1 and PD-1 expressions, respectively. Cancer cells were then treated with ICIs for 6 h, and subsequently co-cultured with Jurkat T in a 1:4 ratio. Cell culture supernatants were collected after 48 h incubation and assessed for IL-2.

Chemosensitivity Assay. Chemosensitivity assay was performed by measuring the synergistic cytotoxicity effect of immune checkpoint inhibitors, together with chemotherapeutic drug, doxorubicin. Cancer cells were plated in 96-well plates (5,000 cells/well) and incubated for 48 h. Cancer cells and Jurkat T cells were pre-treated with IFNγ and PHA/PMA as aforementioned. Cancer cells were then stained with calcein AM (1.5 µM), followed by 2 h treatment with ICIS. The cells were co-cultured for another 24 h in a 1:4 ratio, prior to doxorubicin (5 µM) treatment. The effect of each ICI on cancer cell survival following doxorubicin treatment (2 h) was analyzed based on changes in fluorescent intensity.

Figure 1:
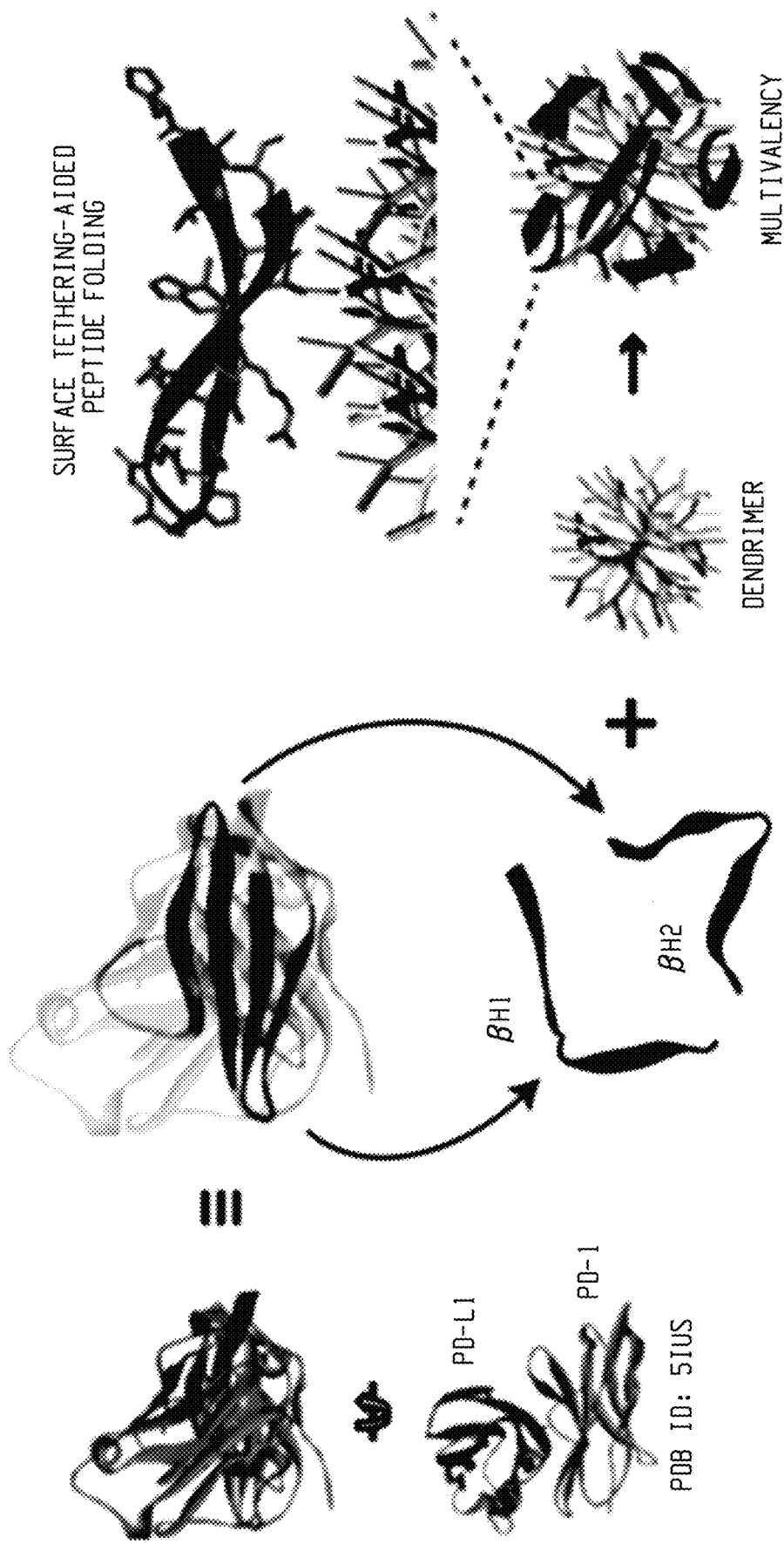
FIG. 1 shows a schematic illustration of the development process of a multivalent dendrimer peptide conjugate as a PD-1/PD-L1 antagonist.
Figure 2:
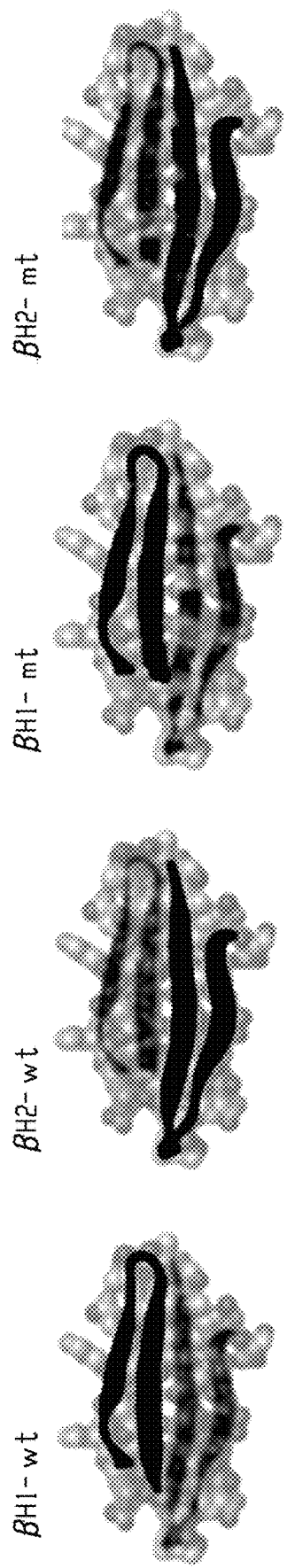
FIG. 2 shows the structures of PD-1, engineered PD-land different peptide structures for targeting PD-L1. SEQ ID NO: 1 is the $\beta H_1$-wt sequence, SEQ ID NO: 2 is the $\beta H_1$-mutant sequence, SEQ ID NO: 3 is the $\beta H_2$-wt sequence, and SEQ ID NO: 4 is the $\beta H_2$-wt sequence. The binding surfaces are highlighted (ribbon).
Figure 3:
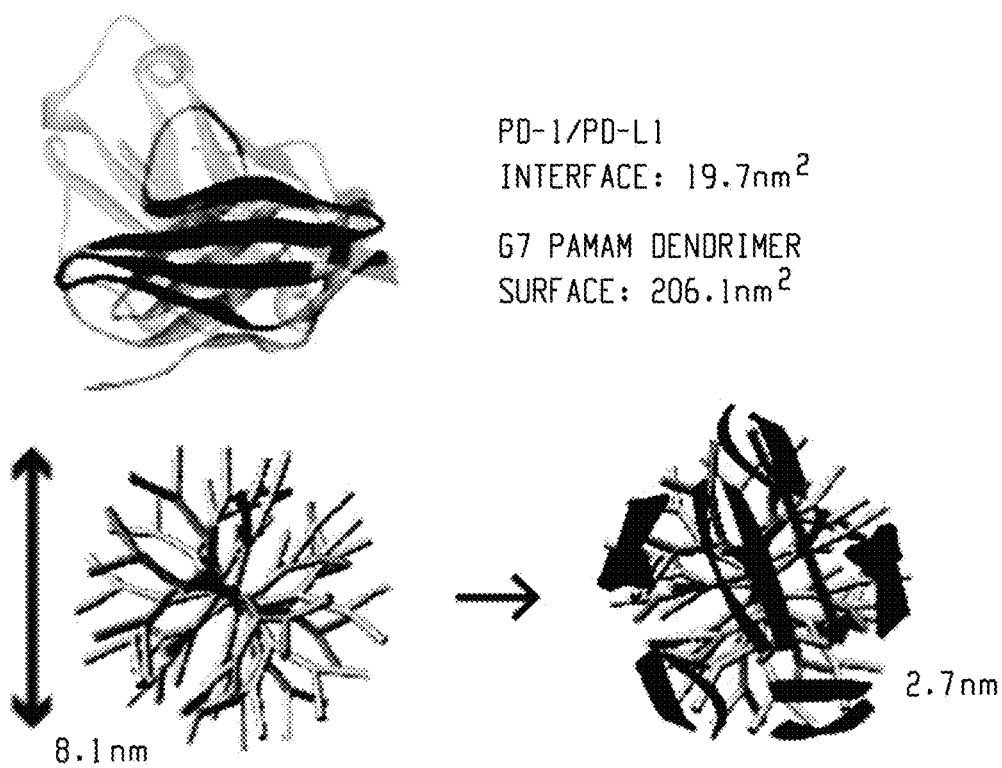
FIG. 3 shows a size comparison among the βH2_mt peptide, G7 PAMAM dendrimer, and PD-1/PD-L1 interface, indicating that the dendrimer surface accommodates multiple peptides being separated by enough spatial distance for binding.
Figure 4:
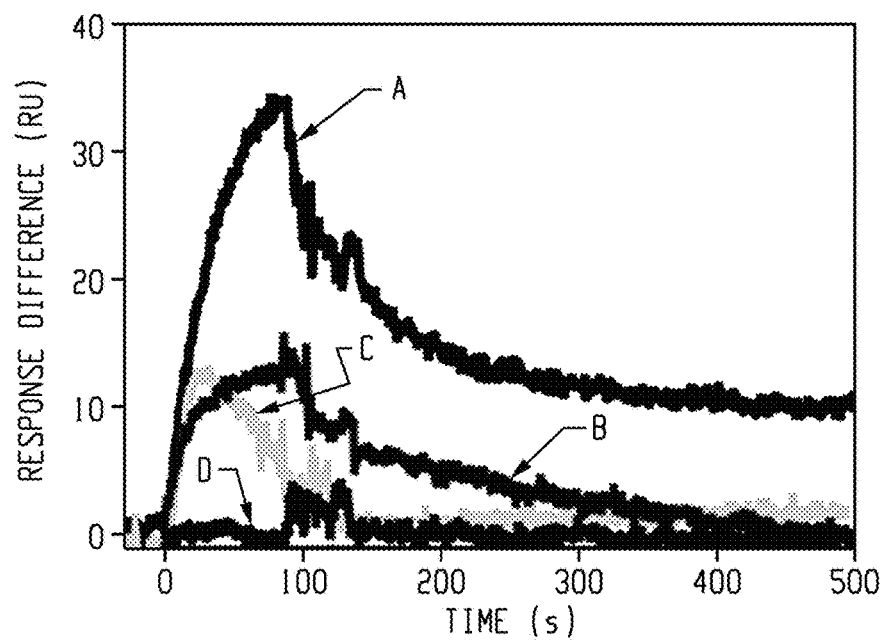
FIG. 4 shows SPR sensorgrams for binding of G7-βH2_mt (A), G7-βH2_wt (B), G7-βH1_mt (C), and fully acetylated dendrimers (D) to immobilized PD-L1 proteins.
Figure 5:
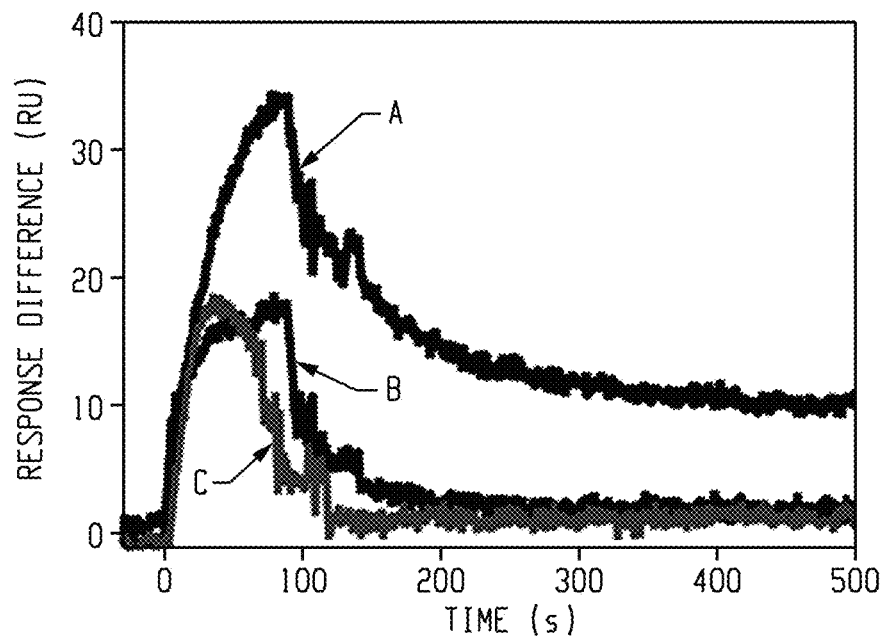
FIG. 5 shows SPR sensorgrams for binding of G7-3H2_mt conjugates using 90% (A), 80% (B), and 60% (C) acetylated dendrimers to PD-L1.
Figure 6:
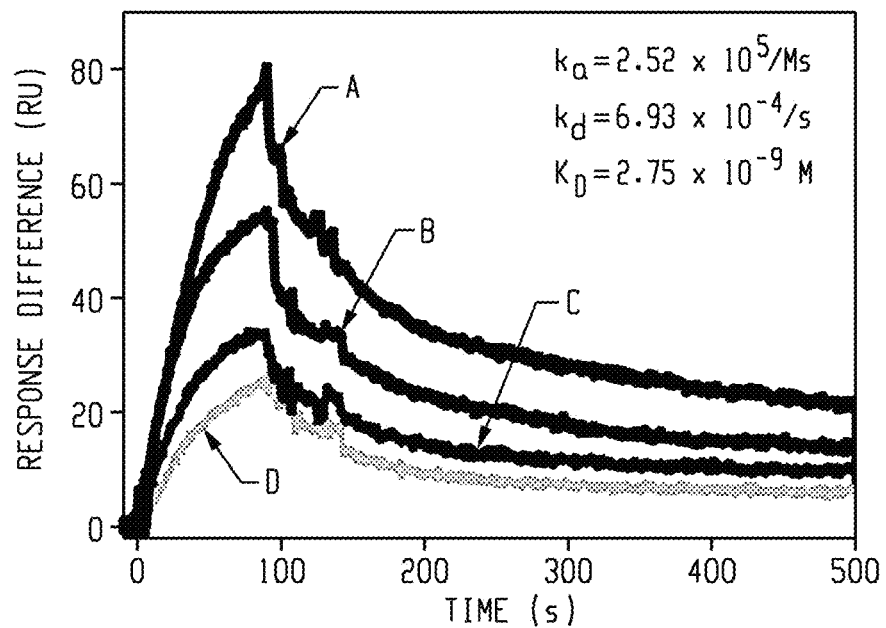
FIG. 6 shows concentration dependent binding kinetics of G7-βH2_mt conjugates to PDL1, with quantitatively measured binding kinetics ($k_a$: association rate constant; $k_d$: dissociation rate constant; $K_D$: equilibrium dissociation constant). Curves A-D represent 45, 90, 180, 270 nM, respectively.
Figure 7:
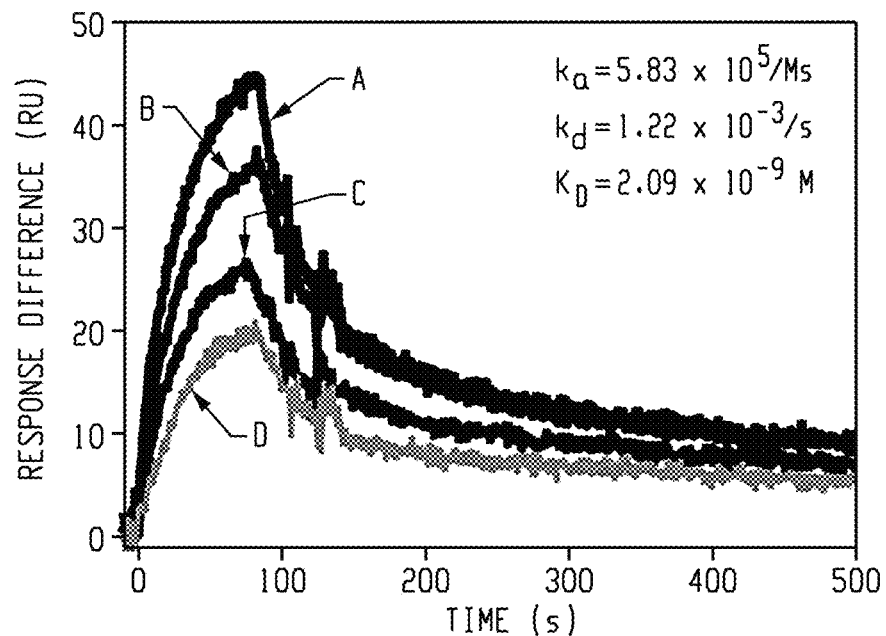
FIG. 7 shows concentration dependent binding kinetics of aPD-L1 antibodies of to PDL1, with quantitatively measured binding kinetics ($k_a$: association rate constant; $k_d$: dissociation rate constant; $K_D$: equilibrium dissociation constant). Curves A-D represent 25, 50, 100, 200 nM, respectively.
Figure 8:
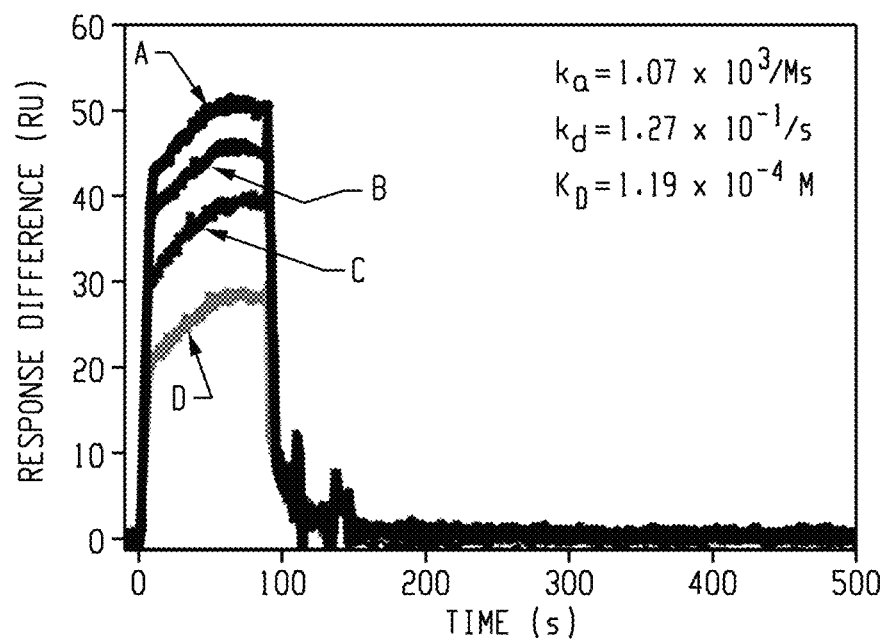
FIG. 8 shows concentration dependent binding kinetics of free βH2_mt peptides to PDL1, with quantitatively measured binding kinetics ($k_a$: association rate constant; $k_d$: dissociation rate constant; $K_D$: equilibrium dissociation constant). Curves A-D represent 17, 25, 33, 42 µM, respectively.
Figure 9:
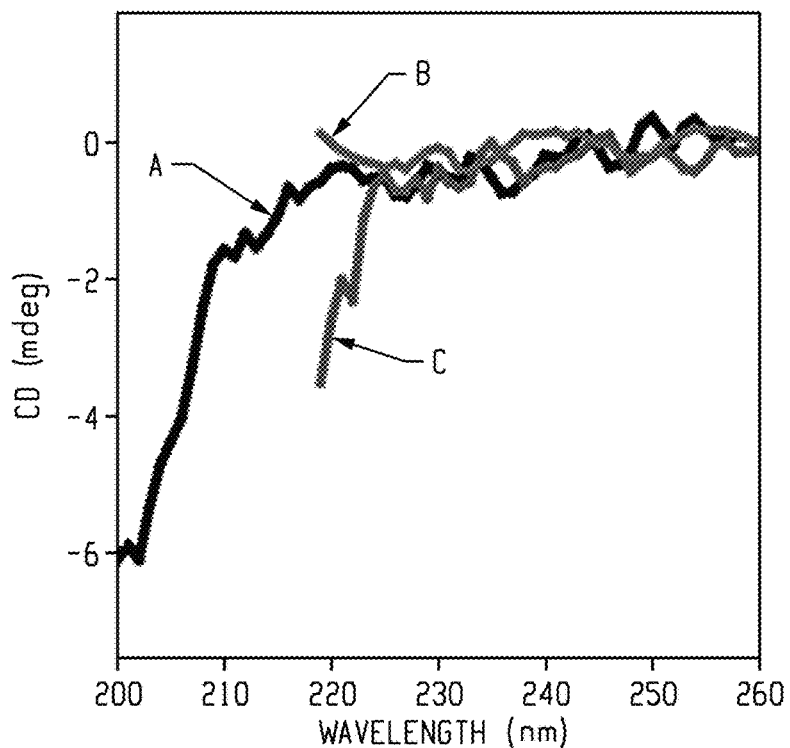
FIG. 9 shows CD spectrum of G7-βH2_mt conjugates (A), H2_mt peptides (B) and fully acetylated dendrimers (C).
Figure 10:
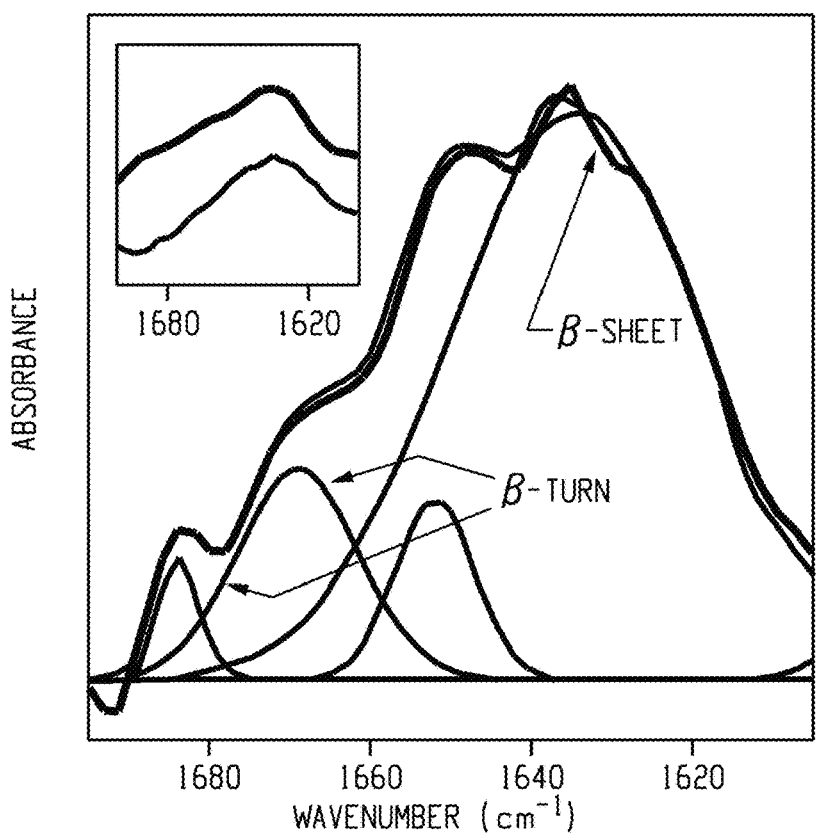
FIG. 10 shows the FTIR spectrum of G7-βH2_mt conjugates and its Fourier self-deconvolution analysis with β-sheet and β-turn labeled. Inset: FTIR spectra of H2_mt peptides (top) and fully acetylated dendrimers (bottom).
Figure 11:
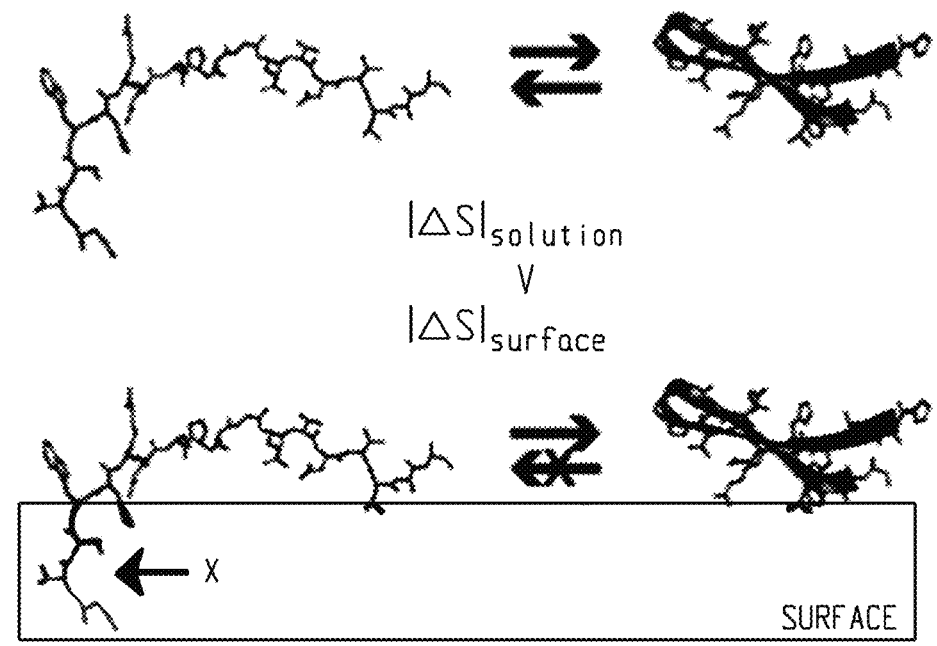
FIG. 11 shows a schematic illustration of the excluded volume effect that decreases entropy cost for peptide folding.
Figure 12:
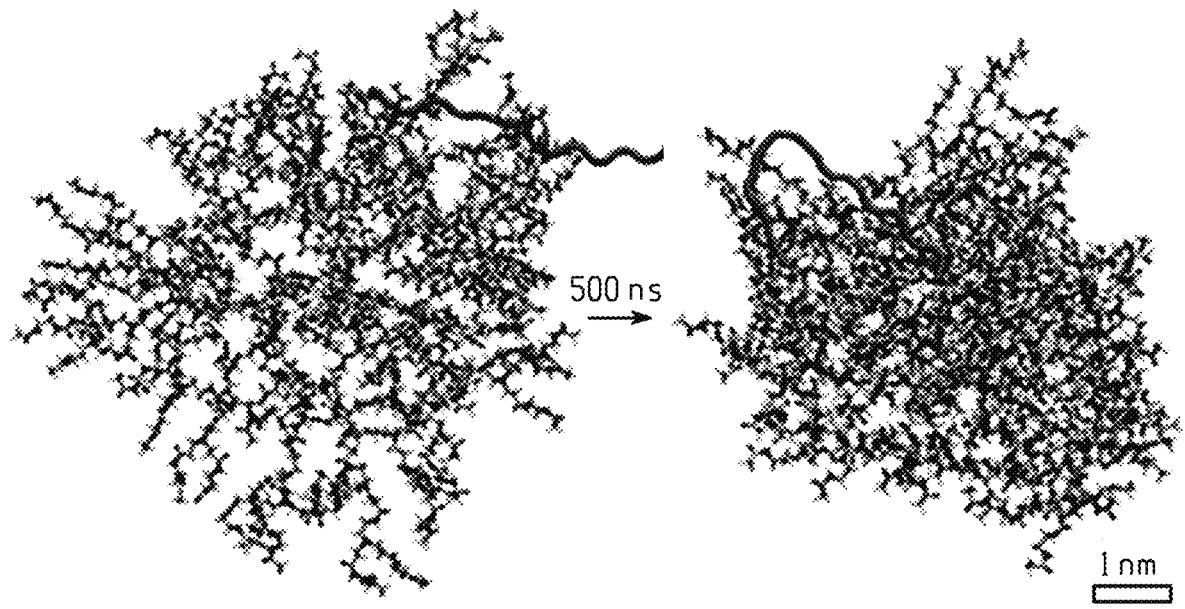
FIG. 12 shows an MD simulation results of the folding behaviors of H2_mt upon conjugation with a G5 PAMAM dendrimer with initially extended βH2_mt (βH2_mt in ribbon, atoms in G5).
Figure 13:
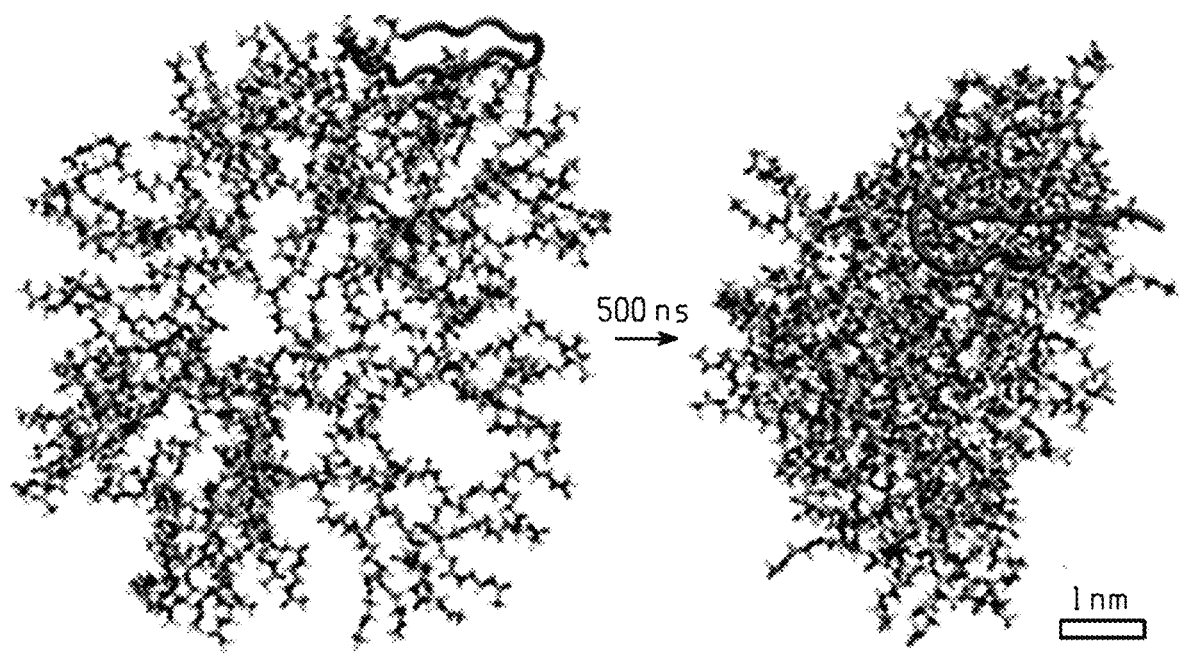
FIG. 13 shows an MD simulation results of the folding behaviors of H2_mt upon conjugation with a G5 PAMAM dendrimer with initially folded βH2_mt (βH2_mt in ribbon, atoms in G5).
Figure 14:
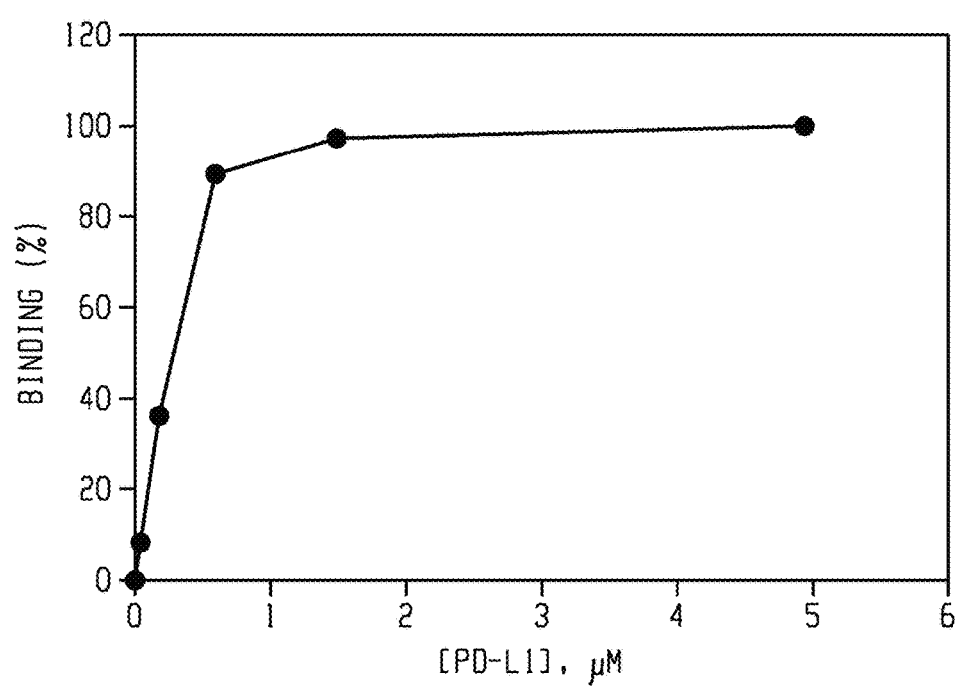
FIG. 14 shows binding of fβH2_mt to PD-L1.
Figure 15:
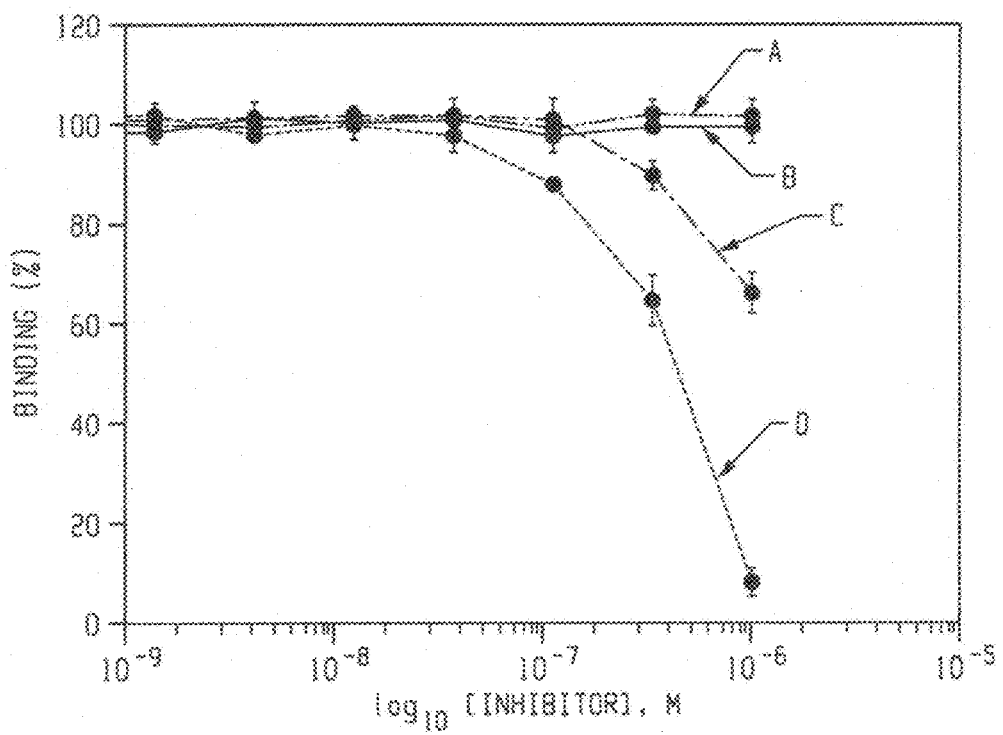
FIG. 15 shows competition assays on G7-βH2_mt (A), aPD-L1 (B), βH2_mt (C), and fully acetylated dendrimer (D) against fβH2_mt/PD-L1 complexes.
Figure 16:
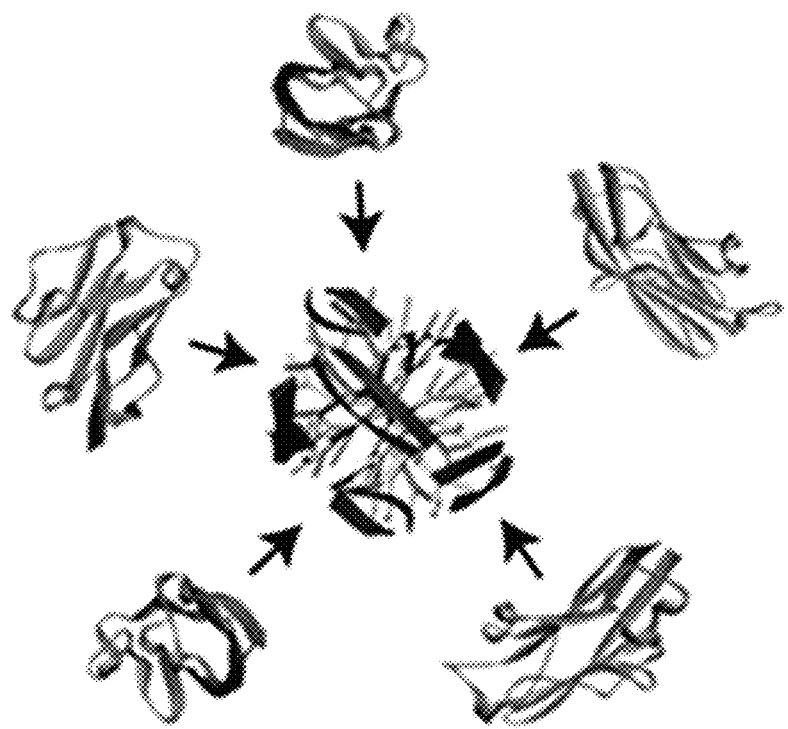
FIG. 16 is an illustration of a G7-βH2_mt conjugate binding to multiple PD-L1 proteins.
Figure 17:
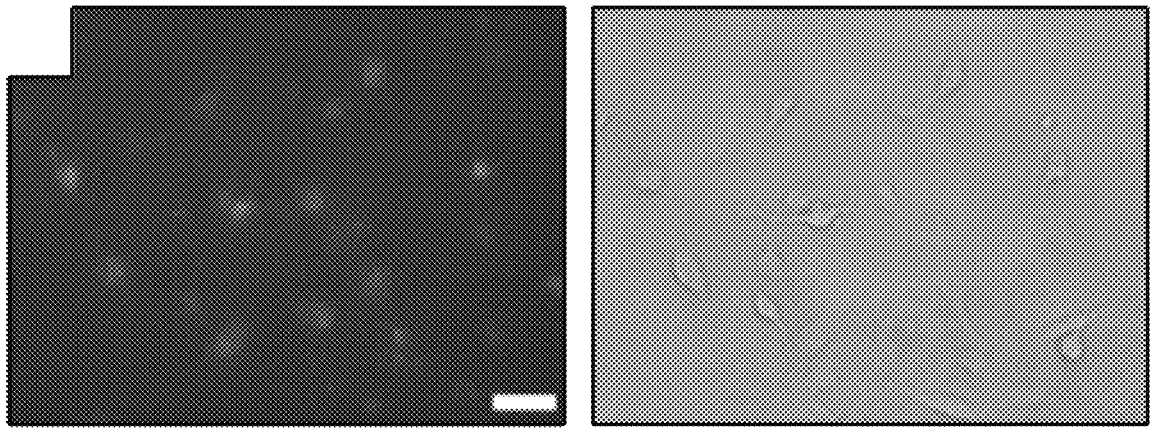
FIG. 17 shows fluorescence microscopy images of 786-O cells treated with G7-βH2_mt for 1 h (fluorescence from Rhodamine, left; bright field image, right), scale bar: 50 m.
Figure 18:
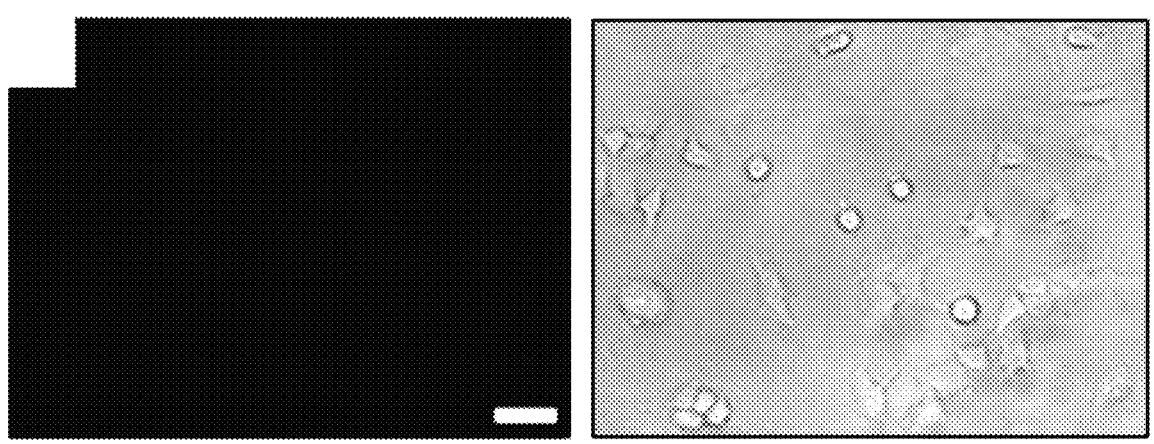
FIG. 18 shows fluorescence microscopy images of MCF-7 cells treated with G7-βH2_mt for 1 h (fluorescence from Rhodamine, left; bright field image, right), scale bar: 50 m.
Figure 19:
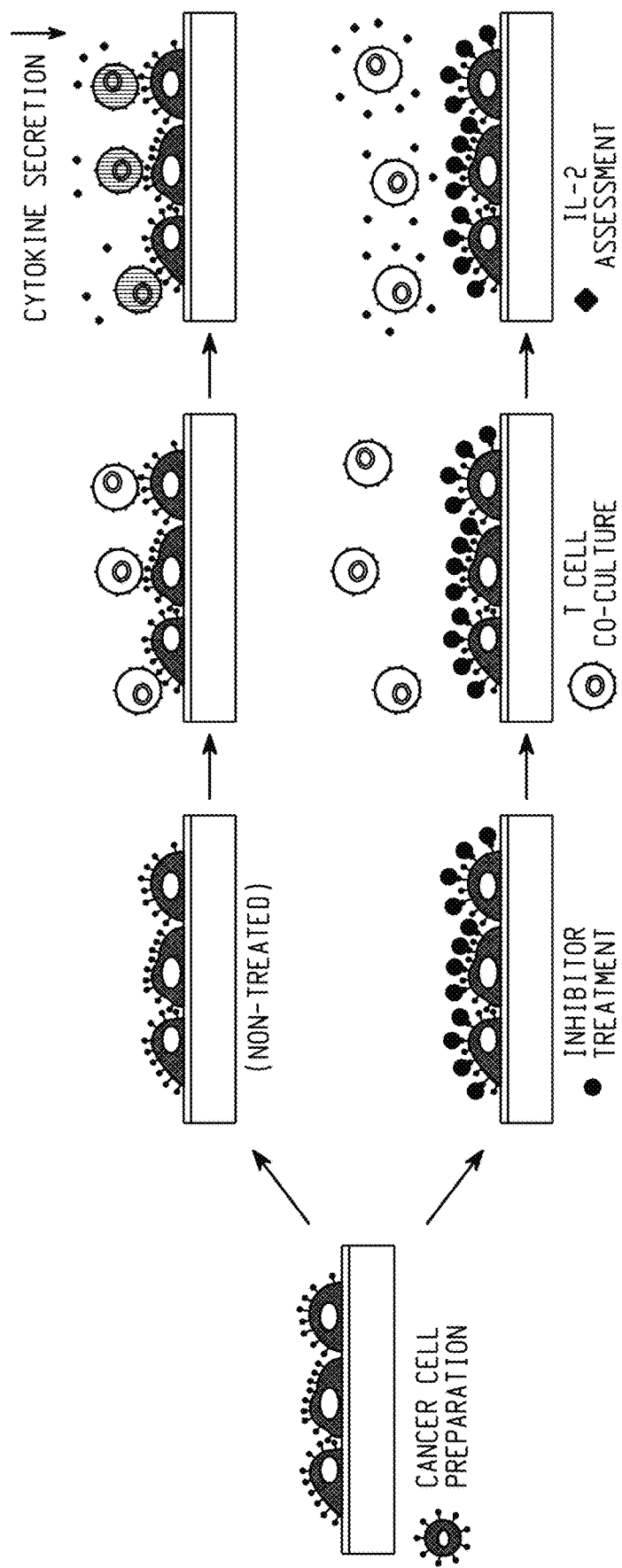
FIG. 19 shows a schematic illustration of immune checkpoint blockade resulting in increased interleukin-2 (IL-2) secretion by Jurkat T cells.
Figure 20:
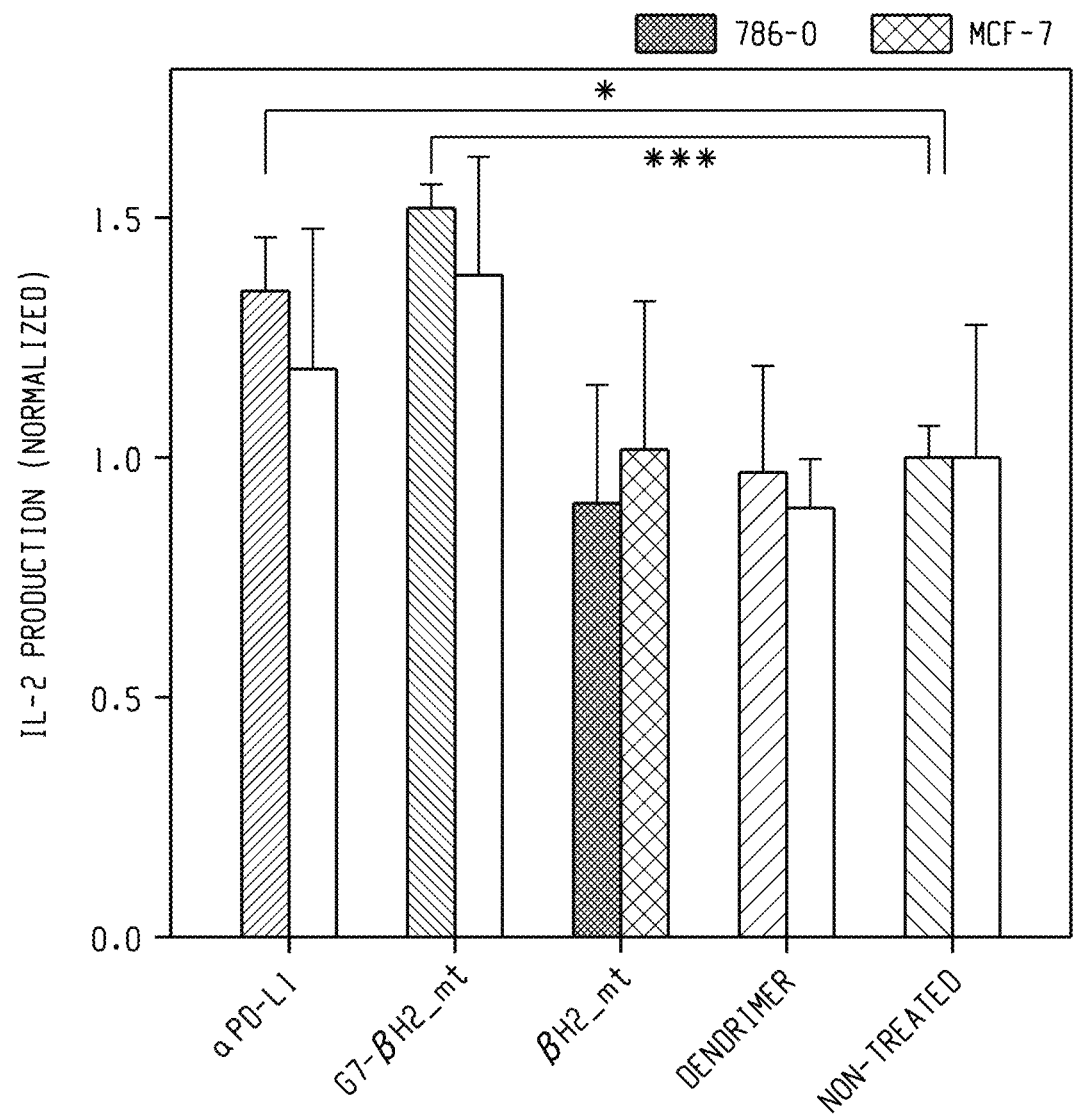
FIG. 20 shows IL-2 secretion from Jurkat T cells co-cultured with 786-O and MCF-7 cells after treated with various groups.
Figure 21:
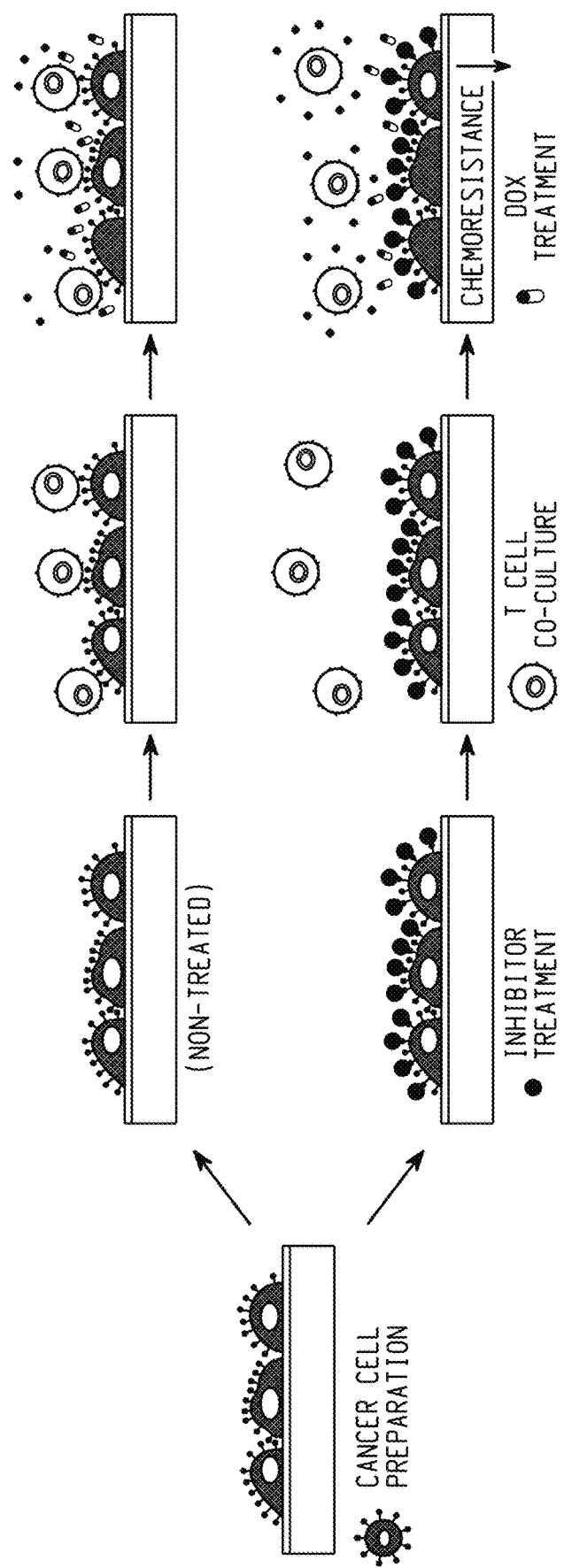
FIG. 21 shows a schematic illustration of immune checkpoint blockade resulting in reduction of cancer cell chemoresistance.
Figure 22:
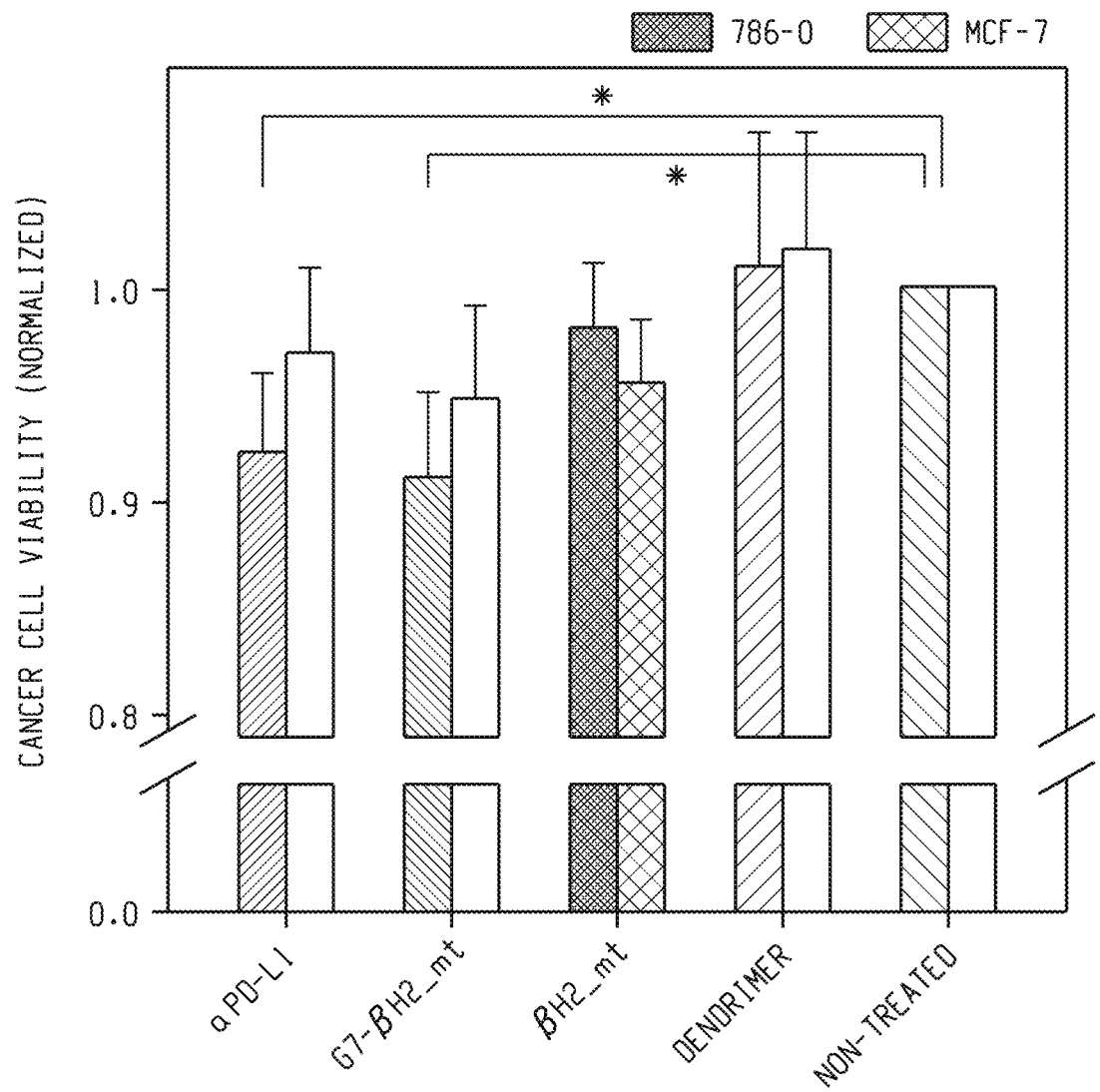
FIG. 22 shows cancer cell viability after doxorubicin (DOX) treatment, demonstrating the chemoresistance of the cancer cells upon incubation with various groups.

Results:

In order to develop a PD-1/PD-L1 peptide inhibitor complex, β-hairpin peptides from the PD-1 surface were identified and engineered through a combination of three synergistic approaches (FIG. 1). First, we used the amino acid composition of an unnatural PD-1 ectodomain optimized to exhibit high PD-L1 affinity. Second, the peptides were conjugated to dendrimer surfaces in a multivalent fashion, thereby enabling cooperative, strong interactions with multiple PD-L1 proteins on tumor cells. Third, the conjugation on a dendrimer surface assisted peptide folding into their native structure, β-hairpin, due to the excluded volume effect and the dendrimer-peptide interactions. Considering the potential synergetic effect of these engineering approaches, we thus hypothesized that this DPC strategy would enable the peptides to outperform natural PD-1 in competitive interaction with PD-L1 for the recovery of antitumor immunity.

To develop PD-L1-targeted DPCs, β-hairpin peptides were synthesized based on the engineered PD-1 ectodomain sequence (βH1_mt and βH2_mt, FIG. 2) and attached to the surface of generation seven (G7) poly(amidoamine) (PAMAM) dendrimers. Before the conjugation, 90% of dendrimer amine groups were acetylated to control the number of attached peptides, given that surface area of G7 PAMAM dendrimers is approximately ten times larger than that of PD-1/PD-L1 interface (FIG. 3). The resulting DPCs, noted as G7-β$H_1$_mt and G7-βH2_mt, were then analyzed using surface plasmon resonance (SPR) to measure their binding kinetics. As shown in FIG. 4, G7-βH2_mt exhibited higher affinity to immobilized PD-L1 proteins than G7-βH1_mt, whereas fully acetylated dendrimers showed no binding response. Additionally, the PD-L1 affinity of G7-βH2_mt was also higher than that of the wildtype βH2-dendrimer conjugate control (G7-βH2_wt), indicating that the engineered PD-1 sequence (βH2_mt) leads to the higher affinity. Hence, we selected H2_mt peptides as the PDL1-targeted ligand and conjugated them to dendrimer surfaces with varying degrees of acetylation to determine effective peptide valency. One can expect that the binding strength as a results of multivalent binding interaction would be proportional to the number of ligand molecules. However, lower PD-L1 affinity was observed for the DPCs with greater numbers of H2_mt peptides (i.e. the DPCs prepared from 80% and 60% acetylated dendrimers) (FIG. 5). These unexpected results are probably attributed to the fact that the optimized spatial distance among ligands plays a key role in achieving stronger binding, rather than a mere increase in the number of ligands, which was also observed elsewhere. These results collectively indicate that G7-βH2_mt prepared from 90% acetylated dendrimers would likely antagonize the PD-1/PD-L1 interaction more effectively than its counterparts, G7-βH1_mt and G7-βH2_wt.

Next, we compared the PD-L1 binding kinetics of G7-βH2_mt with that of anti-PD-L1 (aPD-L1) antibodies and free H2_mt peptides. The SPR analysis revealed that G7-βH2_mt showed five orders of magnitude higher PD-L1 affinity than βH2_mt ($K_D$ of $2.75\times10^{-9}$ vs. $1.19\times10^{-4}$), which is comparable to that of whole aPD-L1 antibody ($K_D$ of $2.09\times10^{-9}$), as shown in FIGS. 6-8 It is noteworthy that the dissociation rate constant ($k_d$) of G7-βH2_mt was decreased by ~180 times, compared to the free peptide, although there were only 30 peptides per dendrimer (data not shown). This non-linear enhancement in binding is characteristic of multivalent binding effect, i.e., a multivalent object has a higher rebinding chance to target molecules than its monovalent counterpart (statistical rebinding mechanism). Interestingly, the association rate constant ($k_a$), which is known to play a minor role in the multivalent binding effect, also increased non-linearly ($2.52\times10^{5}$ vs. $1.07\times10^{3}$). This result implies that other factors, in addition to the multivalent binding, contribute to the significantly enhanced PD-L1 binding of G7-βH2_mt.

To elucidate the mechanism behind the improved binding kinetics of G7-βH2_mt, we investigated the folding structure change of the peptides, which significantly affects their target affinity and selectivity,[20] upon conjugation to dendrimers. FIG. 9 shows the circular dichroism (CD) profile of G7-βH2_mt (red line) where a degree of peptide folding was observed (the negative signal at approximately 220 nm), which is distinct from the typical broad negative CD band centered at 222 nm due to an α-helical structure. In contrast, free H2_mt displayed an almost unfolded random-coil structure (black line), as shown in the strong negative CD band at approximately 200 nm. Note that the CD profiles for dendrimers (both red and gray lines) omitted the signal below 218 nm due to the abundant amide bonds in the dendrimer backbones absorbing far ultraviolet (UV) light. A concentration of 1 M of dendrimers was used to minimize the absorption of low wavelength light by the macromolecules and yet to obtain strong enough signals for data interpretation in a range of 190-230 nm where the secondary structure of peptides is typically characterized.

We then employed the attenuated total reflection-Fourier transform Infrared (ATR-FTIR) to study the folding behaviors of the peptides. As shown in FIG. 10, the FTIR spectra confirmed the presence of random coil and β-sheet (a broad band around 1640 $cm^{-1}$), along with a trace of β-turn structures (weak absorption around 1670 and 1690 $cm^{-1}$), in βH2_mt peptides. In contrast, the FTIR spectrum of G7-βH2_mt displayed the signature of a β-hairpin structure with resolvable absorption at 1634 $cm^{-1}$ for inter-strand vibrational couplings and 1668 and 1683 $cm^{-1}$ for β-turn conformation. Therefore, both of the structural analyses collectively show that the hairpin structure of βH2_mt is stabilized by the dendrimer conjugation. These results are in agreement with several theoretical studies suggesting that surface tethering allows the stabilization of biomolecular structures via the excluded volume effect (FIG. 11), i.e., in the presence of a substrate, conformational freedom of a peptide to be unfolded is limited, resulting in reduced entropy cost for folding.

To support the experimental results, we additionally performed molecular dynamics (MD) simulations using a single βH2_mt peptide-generation five (G5) PAMAM dendrimer conjugate. Note that G5 PAMAM dendrimer, instead of larger G7, was used for efficient computing time. The peptide behaviors on the surface of a dendrimer were compared for 500 ns from initially (1) extended and (2) folded βH2_mt (FIGS. 12 and 13). In contrast to free βH2_mt exhibiting both folded and extended conformations in the solution, the initially extended peptide bent to a folded structure and initially folded βH2_mt stably maintained the folded conformation on the dendrimer surface. Interestingly, the peptide generated various intermolecular forces with the dendrimer surface, including hydrogen bonds, electrostatic interactions, and van der Waals interactions, while maintaining the hairpin structure (data not shown). In general, formation of such molecular interactions with a surface is known to reduce the structural stability of proteins. However, βH2_mt is an isolated peptide segment that is originally exposed to multiple molecular interactions within the entire PD-1 protein structure (data not shown). These molecular interactions seem to contribute to the further stabilization of the peptide molecule in a folded conformation on the dendrimer surface, in addition to the reduced entropy cost described above. The best way to stabilize β-hairpin is the covalent cross-linking of the two strands in a peptide. However, chemical modifications typically complicate the peptide preparation process and, in turn, induce a significant decrease in synthetic yield. The introduction of inter-strand noncovalent binding is another commonly used strategy; however, it requires substantial amino acid substitutions, which potentially affects physicochemical properties of the peptide. On the contrary, our DPC strategy allows to stabilize the hairpin structure of peptides with minimal modifications to the peptide structure. Combined with the multivalent binding advantages endowed from the dendritic nanoparticles, this unique DPC platform presents a novel way to effectively antagonize and target β-sheet-rich protein surfaces.

Next, we investigated the possibility of using G7-βH2_mt as a PD-1/PD-L1 inhibitor. To perform a fluorescence polarization (FP) competition assay, fluorescein-conjugated βH2_mt (fβH2_mt) peptides were synthesized and used to construct target complexes with PD-L1 proteins (FIG. 14). In the competition experiment (fβH2_mt, 10 nM; PD-L1, 2 μM), the complex integrity was not affected by the addition of βH2_mt peptides and fully acetylated dendrimers, whereas G7-βH2_mt resulted in a dose-dependent displacement of fβH2_mt from PD-L1 (FIG. 15). Interestingly, the DPC showed a more effective competitiveness than aPDL1 antibodies despite the slightly lower PD-L1 affinity, which can be attributed to the multivalent ligand display that allows the accommodation of multiple target proteins on a DPC surface (FIG. 16).

To further scrutinize their efficiency, the DPCs were then tested in vitro. As shown in FIGS. 17 and 18, strong cell interactions of G7-βH2_mt with 786-O cells (a PD-L1 overexpressing cell line) were observed using a fluorescence microscope, whereas the DPCs interacted significantly less with MCF-7 cells (with a low level of PD-L1 expression), demonstrating high PD-L1 selectivity of G7-βH2_mt. The in vitro PD-1/PD-L1 inhibitory effect was then assessed by measuring the amount of cytokines (interleukin-2, IL-2) secreted by Jurkat T cells after being co-cultured with the cancer cells, as described elsewhere (FIG. 19). The blockade of PD-1/PD-L1 binding is well known to activate T cells and promote their cytokine production. FIG. 20 shows that G7-βH2_mt effectively inhibited the 786-O/Jurkat T cell interaction, resulting in an increased IL-2 secretion from the T cells by 1.52-fold ($p<0.001$) compared with the non-treated cancer cells, which was even more pronounced than aPD-L1 antibodies that showed a 1.34-fold enhancement ($p=0.011$) only. This could be attributed to the multivalent binding effect of G7-βH2_mt. Note that neither free peptides nor fully acetylated dendrimers induced noticeable IL-2 production.

To corroborate the PD-1/PD-L1 inhibition, we also tested if the DPC treatment can affect chemoresistance of cancer cells, which is proven to be reduced by immune checkpoint blockade in many clinical and pre-clinical studies. A co-culture model using tumor (786-O or MCF-7) and Jurkat T cells was employed to investigate the synergistic cytotoxic effect of doxorubicin (DOX) and G7-βH2_mt (FIG. 21). Cancer cells treated with different PD-L1 antagonists were co-cultured with the T cells, followed by DOX treatment to induce cell death. As shown in FIG. 22, blocking PD-L1 molecules with G7-βH2_mt significantly reduced the chemoresistance of 786-O cells, exhibiting a decreased cell viability by 8.4±3.8%, compared to the cells treated with doxorubicin only ($p=0.022$). G7-βH2_mt was slightly more effective than the aPD-L1 antibodies that induced a 7.2±3.7% cell viability reduction ($p=0.030$). Considering that the free peptides only have a minor effect on the chemoresistance (1.8±2.0% reduction; $p=0.334$) and fully acetylated G7 dendrimers have no cytotoxic effect on the cancer cells, this result provides another layer of evidence that multivalent G7-βH2_mt effectively blocks the PD-1/PDL1 immune checkpoint. MCF-7 cells, expressing a low level of PD-L1, also exhibited a similar tendency, although the differences were not as significant as the high PD-L1 expressing 786-O cells.

In conclusion, we have demonstrated that the DPC approach enables β-hairpin peptides isolated from protein surfaces to be multimerized and conformationally stabilized on nanoscale dendrimers, thereby exhibiting significantly enhanced target affinity. The enhanced binding kinetics was translated into a significant enhancement of in vitro efficiency where the DPCs exhibited dramatically stronger PD-1/PD-L1 inhibitory effect than the free peptides and a comparable level of efficiency to aPD-L1 antibodies. The PD-L1 inhibition using antibodies has already been clinically proven effective in treating several cancer types, such as non-small lung cancer, bladder cancer, and Merkel cell skin cancer. However, the currently approved antagonists based on monoclonal antibodies have limitations due to their high cost and a lack of modularity. Our strategy has potential to address these problems, because the dendrimer-peptide system offers a platform technology that can accommodate not only immunotherapy but other antitumor agents as well. Furthermore, a variety of β-hairpin peptides on many protein surfaces could be compatible with this DPC approach, increasing its potential to be used in diverse biomedical applications. This study provides a newly engineered peptide-nanoparticle platform for effective regulation of protein interactions to tackle various diseases, including immune checkpoint blockade for cancer therapy.

Example 2: Trpzip DPCs

When a β-hairpin is stabilized by Trpzip, the Trp residues are disposed on the same peptide surface (FIG. 25). Hence, surface attachment of the peptide in an appropriate direction prevents the exposure of the Trp cluster and, consequently, minimizes their non-specific contribution in target binding. To develop the Trpzip-DPC hybrid system, the primary structure of pL1 was modified (SEQ ID NO: 4) considering PD-1/PD-L1 complex structure and the dendrimer conjugation process to provide SEQ ID NO: 5 (FIG. 26). Because amino acid residues buried in PD-1 core are irrelevant to PD-L1 binding, we substituted some of them (arginine, aspartate, and leucine) with Trp residues to introduce Trpzip structure. One of the core residues, valine, was additionally substituted with a lysine for the dendrimer conjugation, which determines peptide directionality to expose PD-L1 binding surface and to make the Trp cluster face the nanoparticle surface (pLiTZ). As the nanoparticle scaffold, we selected dendrimers.

Figure 27:
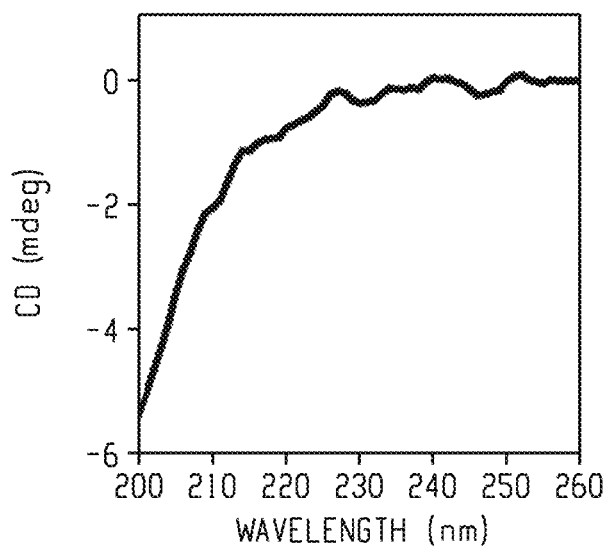
FIG. 27 shows CD spectra of pL1.
Figure 28:
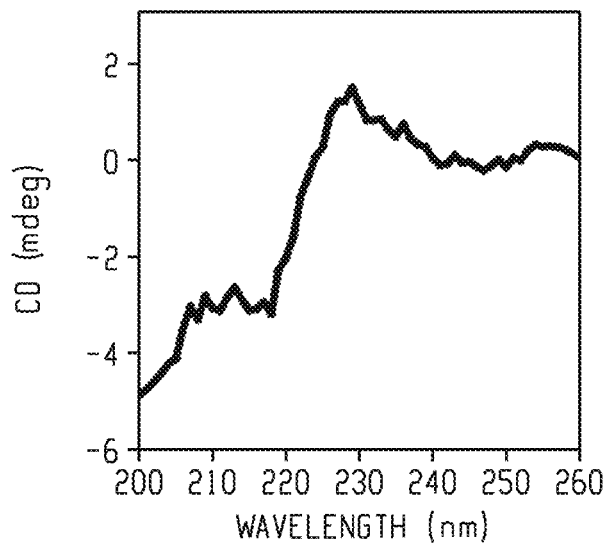
FIG. 28 shows CD spectra of pL1TZ
Figure 29:
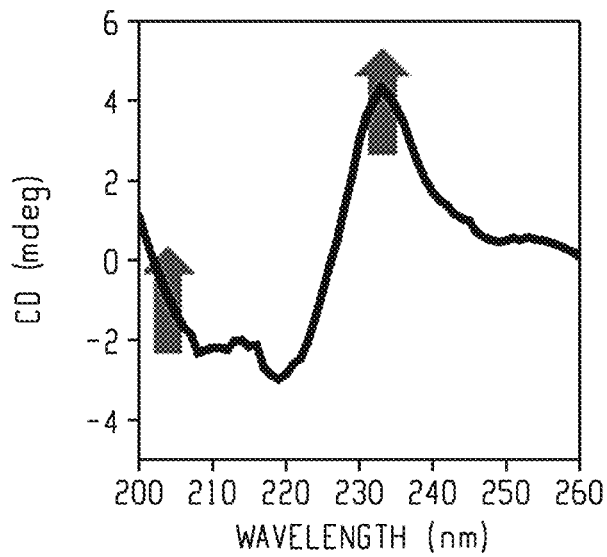
FIG. 29 shows G4-pL1TZ.
Figure 30:
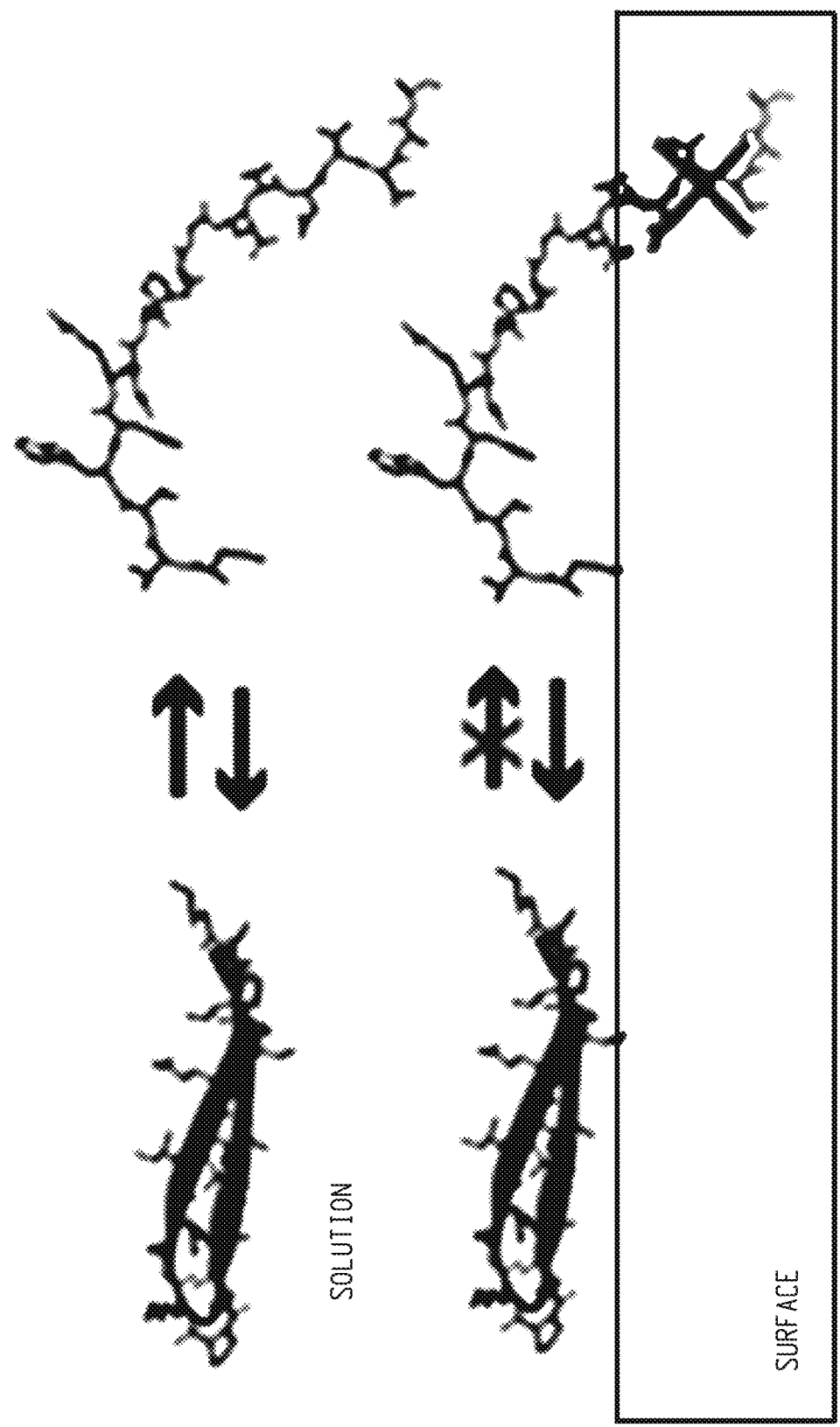
FIG. 30 shows a schematic illustration of the excluded volume effect.
Figure 31A:
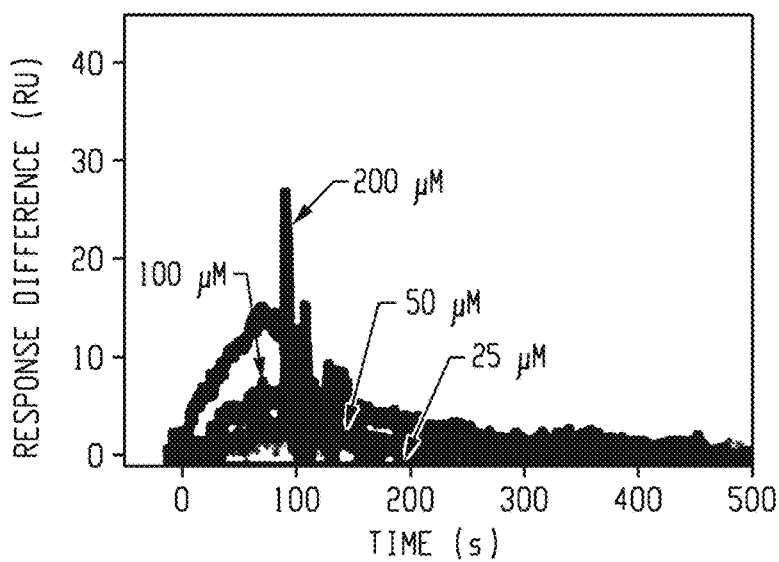
FIG. 31A shows a concentration dependent SPR sensorgram for PD-L1 binding of pL1.
Figure 31B:
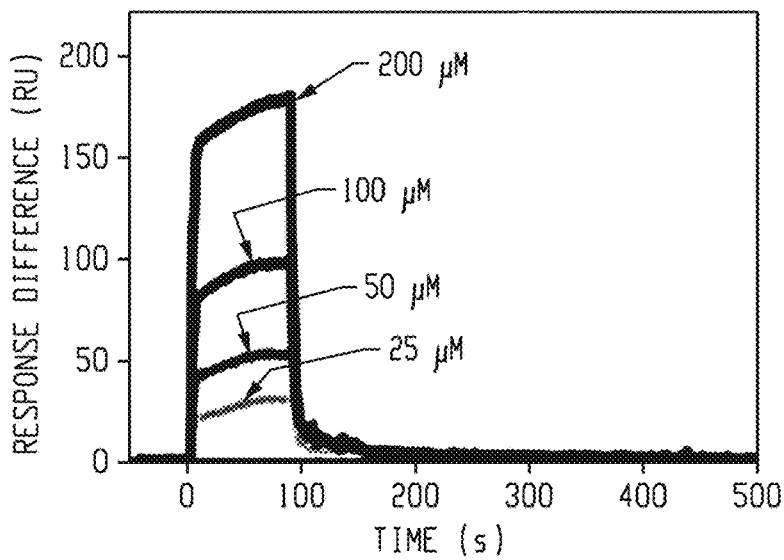
FIG. 31B shows a concentration dependent SPR sensorgram for pL1TZ.
Figure 31C:
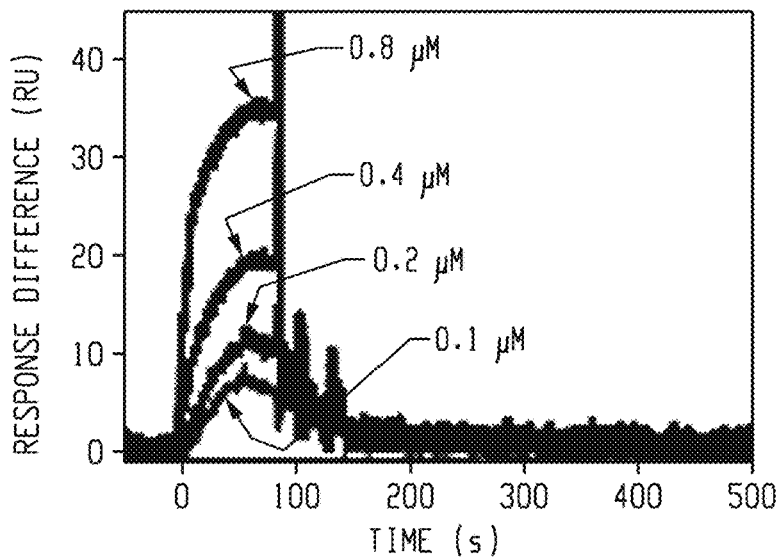
FIG. 31C shows a concentration dependent SPR sensorgram for G7-pL1TZ.
Figure 32:
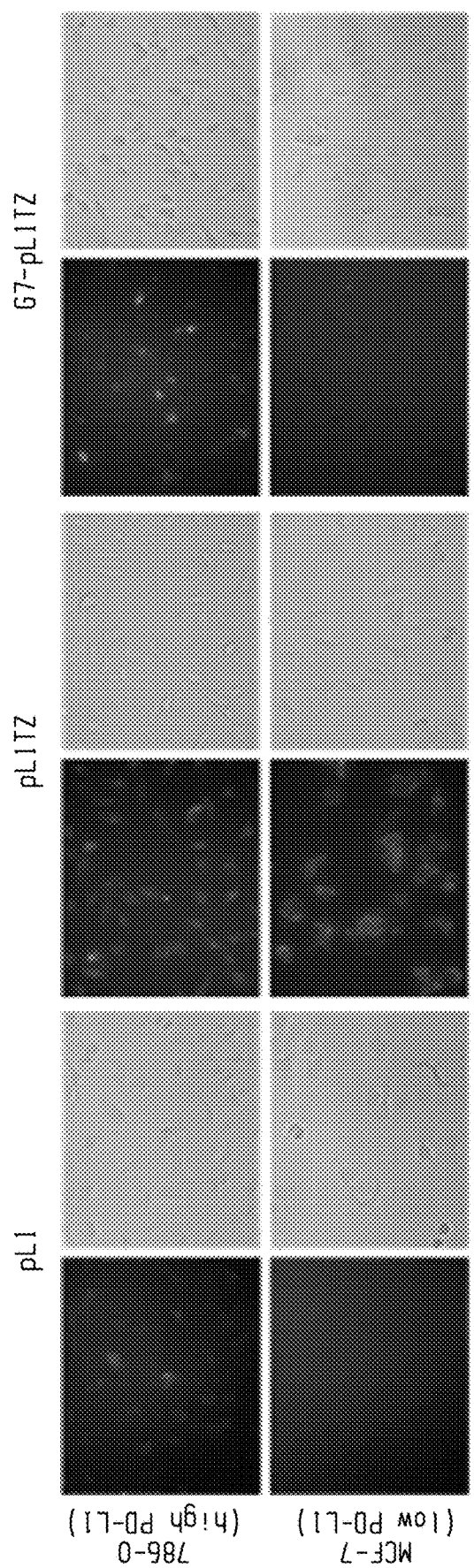
FIG. 32 shows fluorescence microscopy images of 786-O and MCF-7 cells treated with pL1, pL1TZ and G7-pL1TZ for 1 h (fluorescence from Rhodamine, left; bright field image, right).

As shown in FIG. 27, pL1 was found to exist in a random coil structure with a strong negative band at around 200 nm. On the other hand, the CD spectrum of pL1TZ consists of a negative band at 200 nm, a weak shoulder at 215 nm (β-sheet), and a weak positive band at 228 nm (an excitoncoupled band showing interactions between Trp residues), showing partially stabilized β-hairpin structure with the Trpzip formation (FIG. 28). Interestingly, the secondary structure was stabilized a step further when attached to the dendrimer surface, which was verified with the significantly increased CD signal at 200 and 230 nm (FIG. 29). Based on the findings in previous studies, we ascribed this surface-assisted hairpin stabilization to the excluded volume effect: the presence of surface limits conformational space of the unordered structure, which reduces entropy of the unfolded state (FIG. 30). Surface plasmon resonance (SPR) analysis revealed that the stabilized and multimerized PD-L1 binding peptides exhibited highly increased PD-L1 binding affinity compared to the free peptides (FIG. 31). In addition, the DPCs also revealed noticeably enhanced PD-L1 selectivity, concealing the Trp residues in the peptide/dendrimer interfacial space (FIG. 32).

Example 3: The Dendrimer-Peptide Conjugate Improves Treatment Efficacy In Vitro Peptide pPD1 has the sequence IYLCGAISLHPKAK-IEESPGA (SEQ ID NO: 6), which binds mouse PD-L1. The peptide was conjugated to dendrimers via SMCC chemistry through its cysteine (C) group.

Figure 33:
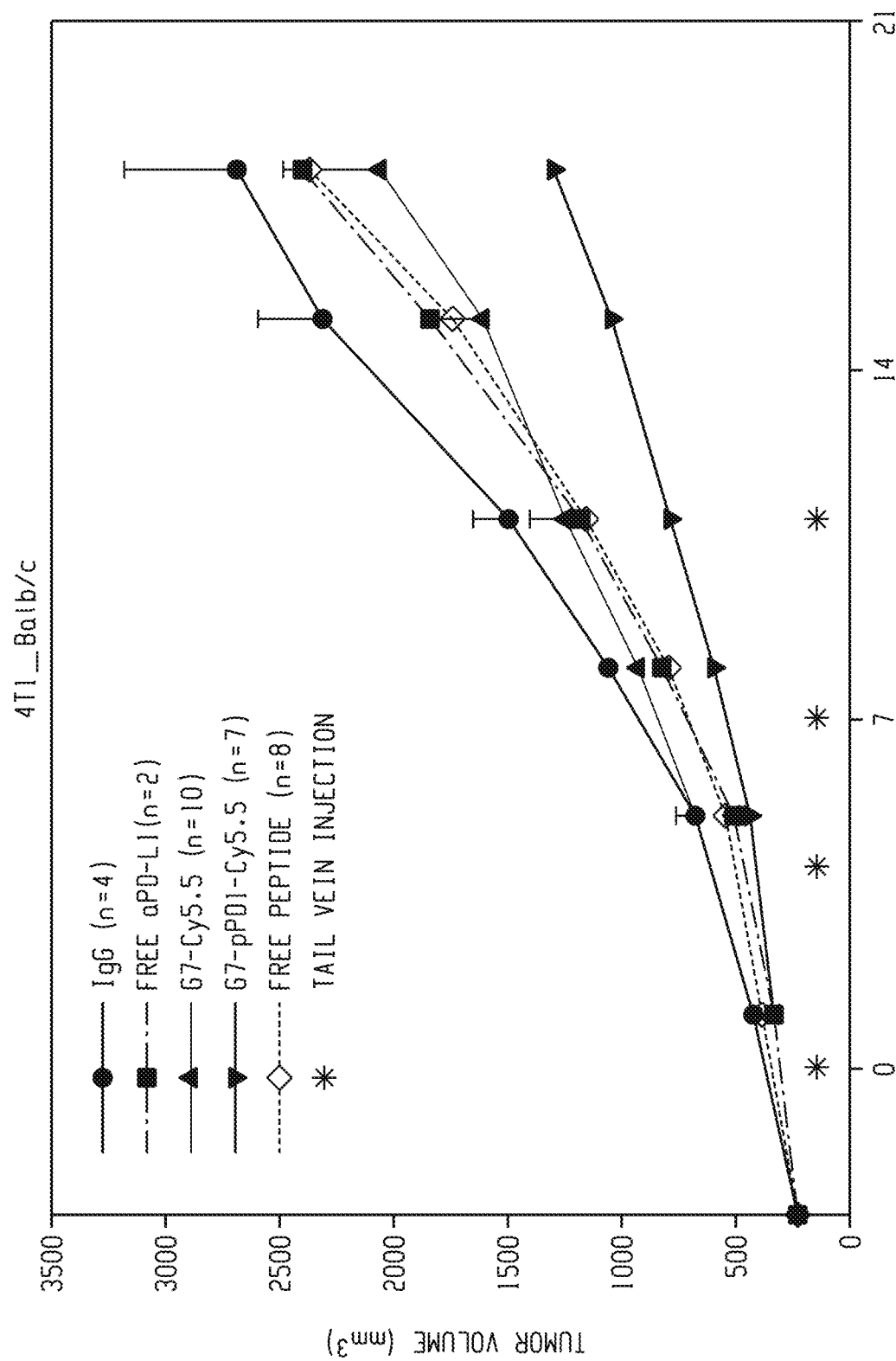
FIG. 33 shows tumor volume as a function of time in Female Balb/c mice inoculated with 4T1 cells limes, and treated with free IgG, free aPD-L1, G7-PMAM dendrimer-Cy-5, G7-PMAM dendrimer-pPD1-peptide-Cy-5, or free pPD1 peptide.
Figure 34:
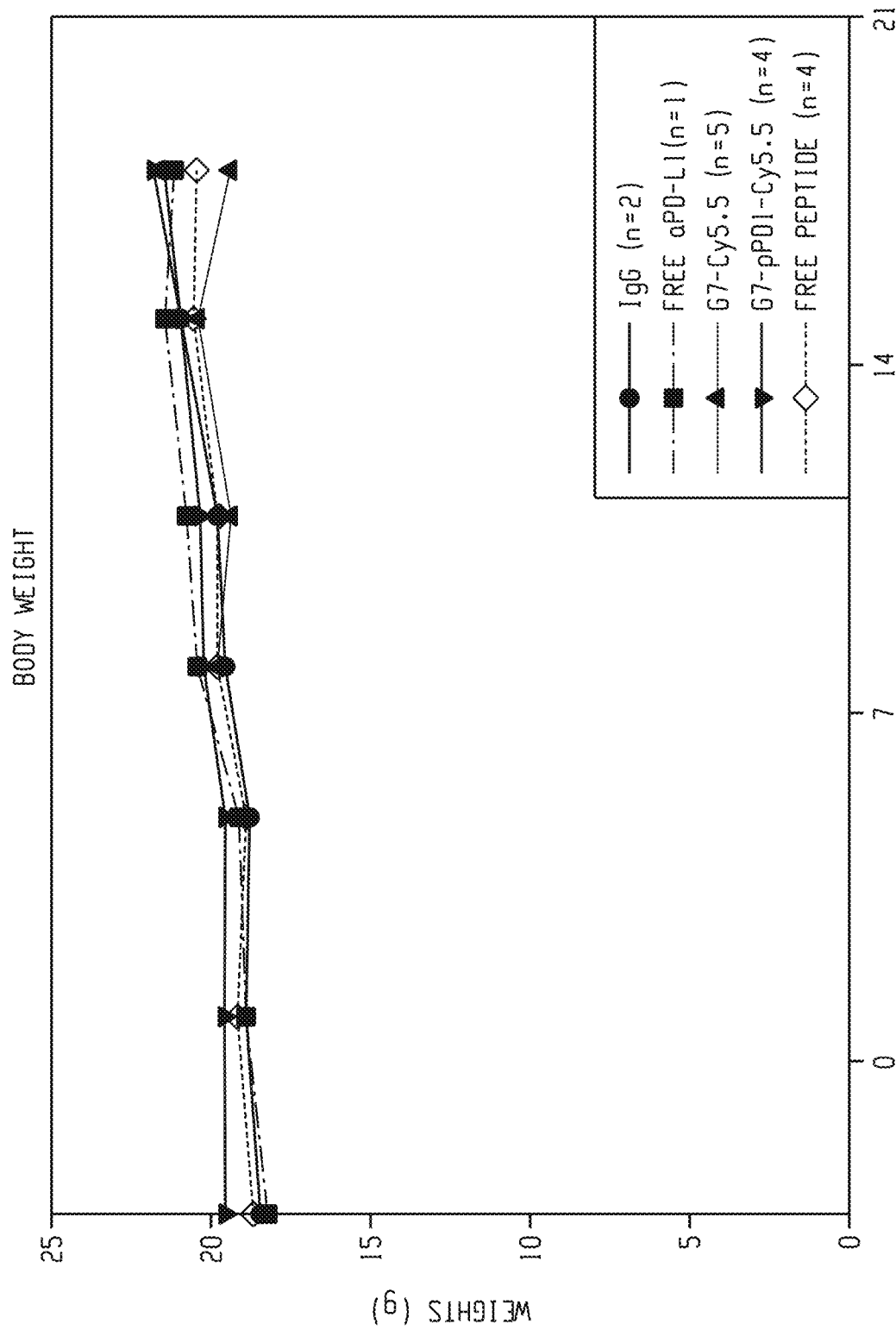
FIG. 34 shows body weight as a function of time in Female Balb/c mice inoculated with 4T1 cells limes, and treated with free IgG, free aPD-L1, G7-PMAM dendrimer-Cy-5, G7-PMAM dendrimer-pPD1-peptide-Cy-5, or free pPD1 peptide.
Figure 35:
FIG. 35 shows tumor bioluminescence for the mice of FIGS. 33 and 34.

Female Balb/c mice (4-6 weeks old) were obtained from Charles River. Animal procedures and maintenance were conducted in accordance with institutional guidelines of University of Wisconsin. 4T1 cell lines were inoculated by subcutaneous injection into the dorsal flank of each mouse and tumor volume was measured using a caliper. When tumors attained a volume of ~250 mm$^3$, mice were randomized into groups and treatment was initiated. 100 μL of reagents were administered by tail vein injection for 3-4 times. Tumor volume and body weight as a function of time are provided in FIGS. 33 and 34. Mice were examined for tumor bioluminescence using an IVIS Spectrum Imaging System (Perkin Elmer). In the data of FIG. 35 error bars represent standard error of means.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. An immunotherapeutic nanoparticle system comprising a multivalent nanoparticle core comprising a plurality of β-hairpin peptides conjugated thereto,
    wherein the multivalent nanoparticle core is a dendrimer, wherein the dendrimer is a poly(amidoamine) (PAMAM) dendrimer, a polyester dendrimer, a polypropyleneimine (PPI) dendrimer, a diaminobutane amine polypropylenimine tetramine (DAB-Am 4) dendrimer, a polypropylamine (POPAM) dendrimer, a polylysine dendrimer, a polyester dendrimer, an iptycene dendrimer, an aliphatic poly(ether) dendrimer, an aromatic polyether dendrimer, or a combination thereof,
    wherein the β-hairpin peptide is a peptide of SEQ ID NO. 1, 2, 3, 4, or 5, and
    wherein the conjugated plurality of β-hairpin peptides provides interaction with multiple copies of an immune checkpoint protein on a tumor cell surface.

2. The immunotherapeutic nanoparticle system of claim 1, further comprising an outer shell encapsulating the multivalent nanoparticle core comprising the plurality of β-hairpin peptides conjugated thereto, wherein the outer shell comprises a liposome or a polymeric shell.

3. A pharmaceutical composition comprising the immunotherapeutic nanoparticle system of claim 1 and a pharmaceutically acceptable excipient.

4. The pharmaceutical composition of claim 3, further comprising a therapeutic, prophylactic or diagnost 5. A method of making the immunotherapeutic nanoparticle system of claim 1, comprising contacting the multivalent nanoparticle cores comprising multiple reactive end groups with a composition comprising the β-hairpin peptides under conditions sufficient to conjugate the plurality of the β-hairpin peptides to the multivalent nanoparticle cores and provide the immunotherapeutic nanoparticle system.

6. The method of claim 5, wherein the reactive end groups comprise dicyclohexylcarbodiimide, diisopropylcarbodiimide, N-(3-Dimethylaminopropyl)-N'-ethylcarbodiimide, 1,1'-carbonyldiimidazole, N-succinimidyl S-acetylthioacetate, N-succinimidyl-S-acetylthiopropionate, 2-Mercaptoethylamine, sulfosuccinimidyl 4-(N-maleimidomethyl)cyclohexane-1-carboxylate, succinimidyl iodoacetate, succinimidyl 3-(2-pyridyldithio)propionate, N-hydroxysuccinimide ester, N-hydroxy sulfosuccinimide ester, N-γ-maleimidobutyryl-oxysulfosuccinimide ester, nitrophenyl ester, tetrafluoro phenyl ester, pentafluorophenyl ester, thiopyridyl ester, thionitrophenyl ester, or a combination thereof.

7. The method of claim 6, further comprising contacting the multivalent nanoparticle cores comprising multiple reactive end groups with a therapeutic, prophylactic or diagnostic agent.

8. The method of claim 5, wherein the hybrid nanoparticle comprises a multivalent polymeric scaffold nanoparticle core with the immune checkpoint inhibitor covalently attached thereto; and an outer shell encapsulating the polymeric scaffold nanoparticle core, wherein the outer shell comprises a liposome or a polymeric shell.

9. An immunotherapy method comprising administering to a subject in need thereof a therapeutically effective amount the nanoparticle system of claim 1.

10. The immunotherapy method of claim 9, wherein the subject is a human cancer patient or a human patient with an immune disorder.

* * * * *

SEQUENCE LISTING

```
<160> NUMBER OF SEQ ID NOS: 5

<210> SEQ ID NO 1
<211> LENGTH: 21
<212> TYPE: PRT
<213> ORGANISM: Artificial Sequence
<220> FEATURE:
<223> OTHER INFORMATION: comment BetaH1- wt sequence

<400> SEQUENCE: 1

Thr Tyr Leu Cys Gly Ala Ile Ser Leu Ala Pro Lys Leu Gln Ile Lys
1               5                   10                  15

Glu Ser Leu Arg Ala
            20
```

```
<210> SEQ ID NO 2
<211> LENGTH: 21
<212> TYPE: PRT
<213> ORGANISM: Artificial Sequence
<220> FEATURE:
<223> OTHER INFORMATION: comment BetaH1- mutant sequence

<400> SEQUENCE: 2

Thr Tyr Val Cys Gly Val Ile Ser Leu Ala Pro Arg Ile Gln Ile Lys
1               5                   10                  15

Glu Ser Leu Arg Ala
            20

<210> SEQ ID NO 3
<211> LENGTH: 18
<212> TYPE: PRT
<213> ORGANISM: Artificial Sequence
<220> FEATURE:
<223> OTHER INFORMATION: comment BetaH2- wt sequence, and

<400> SEQUENCE: 3

Val Leu Asn Trp Tyr Arg Met Ser Pro Ser Asn Gln Thr Asp Arg Lys
1               5                   10                  15

Ala Ala

<210> SEQ ID NO 4
<211> LENGTH: 18
<212> TYPE: PRT
<213> ORGANISM: Artificial Sequence
<220> FEATURE:
<223> OTHER INFORMATION: comment BetaH2 mutant sequence

<400> SEQUENCE: 4

His Val Val Trp His Arg Glu Ser Pro Ser Gly Gln Thr Asp Thr Lys
1               5                   10                  15

Ala Ala

<210> SEQ ID NO 5
<211> LENGTH: 18
<212> TYPE: PRT
<213> ORGANISM: Artificial Sequence
<220> FEATURE:
<223> OTHER INFORMATION: Trp-Zip BetaH2 mutant sequence

<400> SEQUENCE: 5

His Lys Val Trp His Trp Glu Ser Pro Ser Gly Gln Trp Asp Thr Trp
1               5                   10                  15

Ala Ala
```